United States Patent
Liu et al.

(10) Patent No.: US 11,701,317 B2
(45) Date of Patent: Jul. 18, 2023

(54) COSMETIC COMPOSITIONS FOR REMOVING MAKEUP AND METHODS THEREOF

(71) Applicant: L'OREAL, Paris (FR)

(72) Inventors: Tianyi Liu, Springfield, PA (US); Zhengzheng Liao, Cranford, NJ (US); Siva Muthukrishnan, Bridgewater, NJ (US); Ryuji Hara, Westfield, NJ (US)

(73) Assignee: L'OREAL, Paris (FR)

( * ) Notice: Subject to any disclaimer, the term of this patent is extended or adjusted under 35 U.S.C. 154(b) by 175 days.

(21) Appl. No.: 17/210,619

(22) Filed: Mar. 24, 2021

(65) Prior Publication Data
US 2022/0304912 A1    Sep. 29, 2022

(51) Int. Cl.
| | | |
|---|---|---|
| *A61Q 1/14* | (2006.01) | |
| *A61K 8/58* | (2006.01) | |
| *A61K 8/41* | (2006.01) | |
| *A61K 8/34* | (2006.01) | |
| *A61K 8/86* | (2006.01) | |
| *A61K 8/44* | (2006.01) | |
| *A61K 8/37* | (2006.01) | |
| *A61K 8/36* | (2006.01) | |
| *A61K 8/60* | (2006.01) | |

(52) U.S. Cl.
CPC ............ *A61K 8/585* (2013.01); *A61K 8/342* (2013.01); *A61K 8/345* (2013.01); *A61K 8/361* (2013.01); *A61K 8/37* (2013.01); *A61K 8/416* (2013.01); *A61K 8/442* (2013.01); *A61K 8/604* (2013.01); *A61K 8/86* (2013.01); *A61Q 1/14* (2013.01)

(58) Field of Classification Search
CPC ........ A61K 8/585; A61K 8/342; A61K 8/345; A61K 8/361; A61K 8/37; A61K 8/416; A61K 8/442; A61K 8/604; A61K 8/86; A61Q 1/14
USPC .......................................................... 424/62
See application file for complete search history.

(56) References Cited

U.S. PATENT DOCUMENTS

| | | | |
|---|---|---|---|
| 10,105,289 B2 | 10/2018 | Guzman | |
| 2004/0042992 A1 | 3/2004 | Romaine et al. | |
| 2004/0234485 A1* | 11/2004 | Maubru ................... | A61Q 5/02 424/401 |
| 2010/0139704 A1 | 6/2010 | Bernard et al. | |
| 2012/0177712 A1 | 7/2012 | Bhattacharya et al. | |
| 2017/0304173 A1 | 10/2017 | Elder et al. | |
| 2019/0070087 A1 | 3/2019 | Cornwell et al. | |

(Continued)

FOREIGN PATENT DOCUMENTS

| | | |
|---|---|---|
| RU | 2691716 C1 | 6/2019 |
| WO | 2020081624 A1 | 4/2020 |
| WO | 2021104780 A1 | 6/2021 |

OTHER PUBLICATIONS

Preliminary Search Report and Written Opinion dated Mar. 22, 2022 for corresponding French Application No. FR 2107456.

*Primary Examiner* — Eisa B Elhilo
(74) *Attorney, Agent, or Firm* — Polsinelli PC

(57) ABSTRACT

Cosmetic compositions including about 0.1 to about 3 wt. % of a cationic surfactant grafted halloysite compound; about 0.5 to about 10 wt. % of a nonionic surfactant, a cationic surfactant, or a mixture thereof; and water, wherein all weight percentages are based on the total weight of the cosmetic composition. Methods of making and using the cosmetic compositions are also disclosed.

20 Claims, 5 Drawing Sheets

(56) References Cited

U.S. PATENT DOCUMENTS

2019/0183229 A1   6/2019  Gu
2020/0000701 A1   1/2020  Uribe et al.

* cited by examiner

US 11,701,317 B2

COSMETIC COMPOSITIONS FOR REMOVING MAKEUP AND METHODS THEREOF

FIELD OF THE DISCLOSURE

The instant disclosure relates to cosmetic compositions and, particularly, high efficacy makeup removing compositions. Additional aspects of disclosure relate to methods for making and using the cosmetic compositions.

BACKGROUND OF THE DISCLOSURE

There has been a trend toward provided cosmetic products with improved long-lasting characteristics. For example, numerous mascara products have been developed that are waterproof and sweat proof. Many cosmetic products that are designed to be waterproof or sweat proof include substantial amounts of film forming agent and are, therefore, difficult to remove. Therefore, makeup removing products are needed to effectively remove them.

Effective makeup removing products, however, tend to be harsh, can injure the skin, and include non-natural ingredients. Consumers desire cosmetics that have better tolerance and affinity for the skin. Additionally, consumers have become aware and often avoid ingredients that are harmful for the skin. Moreover, those who use makeup remover are likely wearing makeup on a regular basis, and therefore seek the most safe and effective methods for easily removing such makeup.

Accordingly, there is an ongoing need for improved cosmetic compositions that are effective for removing makeup.

SUMMARY OF THE DISCLOSURE

Aspects of the disclosure relate to cosmetic compositions that have a high efficacy of removing makeup compositions. The cosmetic compositions utilize a unique combination of ingredients in specific amounts and ratios to achieve highly desirable properties. The inventors discovered that cosmetic compositions having a unique combination of ingredients and produced under certain process conditions have a high efficacy of removing makeup. Surprisingly, the inventors discovered that the unique combination of ingredients synergistically provided enhanced efficacy for removing makeup. Additionally, it was discovered that certain steps for producing the cosmetic compositions (e.g., mixing the ingredients of the cosmetic compositions at about 50° C. or more until homogenous) attributed to further improved makeup removal efficacy.

The cosmetic compositions according to an aspect of the disclosure typically include:
  (a) about 0.1 to about 3 wt. % of a cationic surfactant grafted halloysite compound;
  (b) about 0.5 to about 10 wt. % of a nonionic surfactant, a cationic surfactant, or a mixture thereof; and
  (c) water,
    wherein all weight percentages are based on the total weight of the cosmetic composition.

The cationic surfactant portion of the cationic surfactant grafted halloysite may be chosen from cetyltrimethylammonium chloride, behentrimonium chloride, brassicamidopropyl dimethylamine, brassicyl isoleucinate esylate, and a mixture thereof. In certain preferred emdoiments, the cationic surfactant portion of the cationic surfactant grafted halloysite is chosen from brassicamidopropyl dimethylamine, brassicyl isoleucinate esylate, and a mixture thereof.

In some embodiments, the cosmetic composition comprises a nonionic surfactant(s) chosen from PEG-55 propylene glycol oleate, PEG-6 propylene glycol caprylate/caprate, PEG-6 caprylic/capric glycerides, PEG-8 propylene glycol cocoate, PEG-25 propylene glycol stearate, glycereth-26 (PEG-26 Glyceryl Ether), PEG-7 glyceryl cocoate, PEG-30 glyceryl cocoate, PEG-75 lanolin, PEG-200 glyceryl stearate, PEG-120 propylene glycol stearate, PEG-120 methyl glucose dioleate, PEG-120 methyl glucose trioleate, PEG-150 pentaerythrityl tetrastearate, PEG hydrogenated castor oil, laureth-2, laureth-3, laureth-4, laureth-7, laureth-9, laureth-12, laureth-23, ceteth-10, steareth-10, steareth-2, steareth-20, steareth-100, beheneth-5, beheneth-5, beheneth-10, oleth-10, pareth alcohols, trideceth-10, trideceth-12, C12-13 pareth-3, C12-13 pareth-23, C11-15 pareth-7, polysorbate-80, polysobate-20, PPG-5 ceteth-20, polyglyceryl-6 caprate, caprylyl/capryl glycoside, poloxamer 182, poloxamer 184, and a mixture thereof. Preferably, the nonionic surfactant is chosen from PEG-6 caprylic/capric glycerides, steareth-20, polyglyceryl-6 caprate, caprylyl/capryl glycoside, poloxamer 182, poloxamer 184, PEG-7 glyceryl cocoate, and a mixture thereof.

The cosmetic composition may include a cationic surfactant chosen from polyaminopropyl biguanide, dodecyltrimethylammonium bromide, hexadecyltrimethylammonium bromide, mytrimonium bromide, and a mixture thereof. In at least one case, the cationic surfactant is mytrimonium bromide. Further non-limiting examples of cationic surfactant chosen from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, stearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidam idopropyidiethylamine, arachidamidoethyidiethylamine, arachidamidoethyidimethylamine, and a mixture thereof.

Additionally or alternatively, the cosmetic composition may comprise an amphoteric surfactant chosen from disodium cocoamphodiacetate, disodium lauroamphodiacetate, disodium caprylamphodiacetate, disodium caprylamphodiacetate, disodium cocoamphodipropionate, disodium lauroamphodipropionate, disodium caprylampho-dipropionate, disodium caprylomphodipropionate, lauroamphodipropionic acid, cocoamphodipropionic acid, and a mixture thereof.

The cosmetic composition may further include about 0.1 to about 20 wt. % of a polyol. The polyol may be chosen from glycerin, propylene glycol, butylene glycol, pentylene glycol, hexylene glycol, and a mixture thereof.

In some instances, the cosmetic composition is substantially free of oil. The cosmetic composition may, additionally or alternatively, be substantially free of anionic surfactants. Preferably, the cosmetic composition is prepared by mixing all of the ingredients at a temperature of about 50° C. or more until homogenous. Additionally or alternatively, the cosmetic composition may be formulated to have micelles.

According to another aspect of the disclosure, a method for removing makeup typically comprises:

(I) applying a cosmetic composition to a layer of makeup on a keratinous substrate, the cosmetic composition comprising:
(a) about 0.1 to about 3 wt. % of a cationic surfactant grafted halloysite compound;
(b) about 0.5 to about 10 wt. % of a nonionic surfactant, a cationic surfactant, or a mixture thereof; and
(c) water, wherein all weight percentages are based on the total weight of the cosmetic composition, and
(II) removing at least a portion of the cosmetic composition.

Preferably, the cationic surfactant portion of the cationic surfactant grafted halloysite compound is chosen from cetyltrimethylammonium chloride, behentrimonium chloride, brassicamidopropyl dimethylamine, brassicyl isoleucinate esylate, and a mixture thereof. In some instances, the cationic surfactant portion of the cationic surfactant grafted halloysite is chosen from brassicamidopropyl dimethylamine, brassicyl isoleucinate esylate, and a mixture thereof. Additionally or alternatively, the cosmetic composition may comprise a nonionic surfactant chosen from PEG-6 caprylic/capric glycerides, steareth-20, polyglyceryl-6 caprate, caprylyl/capryl glycoside, poloxamer 182, poloxamer 184, PEG-7 glyceryl cocoate, and a mixture thereof.

In accordance with a further aspect of the disclosure, a method for producing a cosmetic composition comprises:
(I) mixing a composition at a temperature of about 50° C. or more until homogenous, wherein the composition comprises:
(a) about 0.1 to about 3 wt. % of a cationic surfactant grafted halloysite compound;
(b) about 0.5 to about 10 wt. % of a nonionic surfactant, a cationic surfactant, or a mixture thereof; and
(c) water, wherein all weight percentages are based on the total weight of the cosmetic composition, and
(II) cooling the composition.

In a preferred embodiment, the composition is mixed at a temperature of about 50 to about 95° C.

BRIEF DESCRIPTION OF THE FIGURES

Implementation of the present technology will now be described, by way of example only, with reference to the attached figures, wherein.

Figure 1:
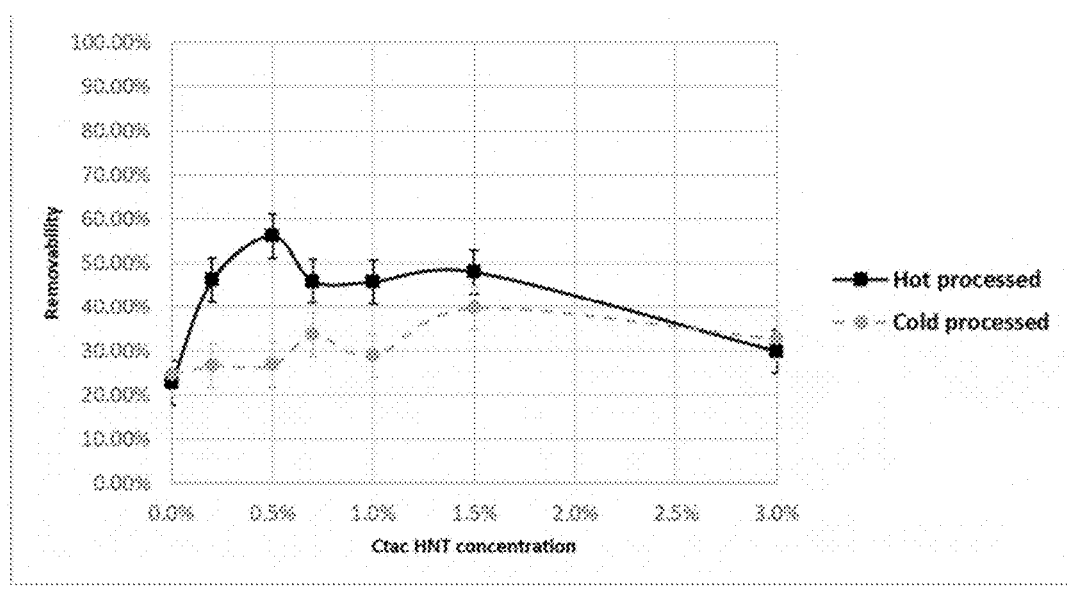
FIG. 1 is a graph illustrating the change in removability for non-limiting exemplary compositions produced under different temperatures according to aspects of the disclosure.

It should be understood that the various aspects are not limited to the arrangements and instrumentality shown in the drawings.

DETAILED DESCRIPTION OF THE DISCLOSURE

Aspects of the disclosure relate to cosmetic compositions that have a high efficacy of removing makeup compositions.

Advantageously, the cosmetic compositions provide a high efficacy for removing makeup while not requiring a significant amount of oil. For example, certain embodiments of the cosmetic composition provide high efficacy for removing makeup while simultaneously being substantially free of or free of oil.

The inventors discovered that cosmetic compositions having a unique combination of ingredients and produced under certain process conditions have a high efficacy of removing makeup. Surprisingly, the inventors discovered that the unique combination of ingredients in certain amounts synergistically provided enhanced efficacy for removing makeup. Additionally, it was discovered that certain steps for producing the cosmetic compositions (e.g., mixing the ingredients of the cosmetic compositions at a temperature of about 50° C. or more until homogenous) attributed to further improved makeup removal efficacy.

The cosmetic compositions according to an aspect of the disclosure typically include:
(a) about 0.1 to about 3 wt. % of a cationic surfactant grafted halloysite compound;
(b) about 0.5 to about 10 wt. % of a nonionic surfactant, a cationic surfactant, or a mixture thereof; and
(c) water,
wherein all weight percentages are based on the total weight of the cosmetic composition.

It was surprisingly discovered that the unique combination of ingredients and specific processing conditions yields synergistic increases in the efficacy of the cosmetic composition for removing makeup. For example, combining and heating a mixture of the ingredients of the cosmetic composition to a temperature of about 50° C. or more significantly enhanced the efficacy of the cosmetic composition for removing makeup. In some embodiments, the mixture of ingredients of the cosmetic composition is heated to a temperature of about 50° C. to about 120° C., about 50° C. to about 100° C., about 50° C. to about 95° C., about 50° C. to about 90° C., about 50° C. to about 85° C., about 50° C. to about 80° C., about 50° C. to about 75° C., about 50° C. to about 70° C., about 50° C. to about 65° C., or about 50° C. to about 60° C.; about 55° C. to about 120° C., about 55° C. to about 100° C., about 55° C. to about 95° C., about 55° C. to about 90° C., about 55° C. to about 85° C., about 55° C. to about 80° C., about 55° C. to about 75° C., about 55° C. to about 70° C., about 55° C. to about 65° C.; about 60° C. to about 120° C., about 60° C. to about 100° C., about 60° C. to about 95° C., about 60° C. to about 90° C., about 60° C. to about 85° C., about 60° C. to about 80° C., about 60° C. to about 75° C., or about 60° C. to about 70° C., including any ranges and subranges therebetween. Although all of the ingredients may be heated to a temperature in the aforementioned ranges, in some embodiments less than all of the ingredients are heated to a temperature in the aforementioned ranges. For example, water may be added to the mixture of ingredients for the cosmetic composition after heating to quantum satis (Q.S.) in order to achieve the expected weight of the cosmetic composition and/or account for evaporation.

The mixture of ingredients of the cosmetic composition may be maintained at a temperature within one of the aforementioned ranges until the mixture is homogenous. For example, the mixture of ingredients may be heated to and/or maintained at temperatures within one of the aforementioned ranges while being mixed, stirred, or the like. In some cases, the mixture of ingredients of the cosmetic composition may be maintained at a temperature within one of the aforementioned ranges for about 1 minute or more, about 5 minutes or more, about 10 minutes or more, about 15 minutes or more, about 20 minutes or more, about 25 minutes or more, about 30 minutes or more, about 35 minutes or more, about 45 minutes or more, about 55 minutes or more, about 65 minutes or more, about 75 minutes or more, or about 90 minutes or more.

Aspects of the instant disclosure enable the cosmetic compositions to be formulated with reduced amounts of oil. For example, the cosmetic compositions may include about 20 wt. % or less, about 15 wt. % or less, about 10 wt. % or less, about 8 wt. % or less, about 6 wt. % or less, about 5 wt. % or less, about 4 wt. % or less, about 3 wt. % or less, about 2 wt. % or less, or about 1 wt. % or less of oil, based on the total weight of the cosmetic composition. In some cases, the cosmetic composition is substantially free or free of an oil.

Additionally or alternatively, the cosmetic composition may have a reduced amount of anionic surfactants. For instance, the cosmetic composition may have about 10 wt. % or less, about 8 wt. % or less, about 6 wt. % or less, about 5 wt. % or less, about 4 wt. % or less, about 3 wt. % or less, about 2 wt. % or less, or about 1 wt. % or less of anionic surfactants, based on the total weight of the cosmetic composition. In some embodiments, the cosmetic composition is substantially free or free of an anionic surfactants.

The cosmetic compositions may, in some instances, include micelles. The micelles may be formed from the cationic surfactant grafted halloysite compound, solely or in conjunction with other ingredients/components of the cosmetic composition.

Suitable components, such as those listed below, may be included or excluded from the formulations for the cosmetic compositions depending on the specific combination of other components, the form of the cosmetic composition, and/or the use of the cosmetic composition.

Cationic Surfactant Grafted Halloysite Compound(s)

The cosmetic compositions include cationic surfactant grafted halloysite compound(s) typically in an amount of about 0.1 to about 3 wt. %, based on the total weight of the cosmetic compositions. For example, the total amount of cationic surfactant grafted halloysite compound(s) may be from about 0.1 to about 3 wt. %, about 0.1 to about 2.95 wt. %, about 0.1 to about 2.75 wt. %, about 0.1 to about 2.5 wt. %, about 0.1 to about 2.25 wt. %, about 0.1 to about 2 wt. %, about 0.1 to about 1.75 wt. %, about 0.1 to about 1.5 wt. %, about 0.1 to about 1.25 wt. %; about 0.2 up to about 3 wt. %, about 0.2 to about 2.95 wt. %, about 0.2 to about 2.75 wt. %, about 0.2 to about 2.5 wt. %, about 0.2 to about 2.25 wt. %, about 0.2 to about 2 wt. %, about 0.2 to about 1.75 wt. %, about 0.2 to about 1.5 wt. %, about 0.2 to about 1.25 wt. %; about 0.3 to about 3 wt. %, about 0.3 to about 2.95 wt. %, about 0.3 to about 2.75 wt. %, about 0.3 to about 2.5 wt. %, about 0.3 to about 2.25 wt. %, about 0.3 to about 2 wt. %, about 0.3 to about 1.75 wt. %, about 0.3 to about 1.5 wt. %, about 0.3 to about 1.25 wt. %; about 0.5 to about 3 wt. %, about 0.5 to about 2.95 wt. %, about 0.5 to about 2.75 wt. %, about 0.5 to about 2.5 wt. %, about 0.5 to about 2.25 wt. %, about 0.5 to about 2 wt. %, about 0.5 to about 1.75 wt. %, about 0.5 to about 1.5 wt. %, about 0.5 to about 1.25 wt. %, including ranges and subranges therebetween, based on the total weight of the cosmetic composition.

The halloysite portion of the cationic surfactant grafted halloysite compound(s) may have a composition generally represented by $Al_2Si_2O_5(OH)_4$. Additionally or alternatively, the halloysite portion may have a nanotube configuration. The outer surface of the halloysite portion may comprises a silicate $SiO_2^-$ layer, while the inner surface may comprise an alumina $Al_2O_3^+$ layer. In some cases, the halloysite may have a hollow nanotubular structure, in which the inner diameter is about 30 to 250 nm and the length is about 0.2 to 0.4 μm. Desirably, halloysite is a natural mineral harmless to the human body, and thus there are no environmental problems and no harm to the human body.

The cationic surfactant grafted halloysite compound generally has a cationic surfactant portion and a halloysite portion. The cationic surfactant portion is preferably cetyltrimethylammonium chloride, behentrimonium chloride, brassicamidopropyl dimethylamine, and/or brassicyl isoleucinate esylate. In some embodiments, the cationic portion of the cationic surfactant grafted halloysite is cetyltrimethylammonium chloride and/or behentrimonium chloride.

Non-limiting examples of additional cationic surfactants that may, in some cases, be the cationic surfactant portion of the cationic surfactant grafted halloysite compound(s) include cetrimonium chloride, stearimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, stearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidam idopropyidiethylamine, arachidamidoethyidiethylamine, arachidamidoethyidimethylamine, and a mixture thereof. In some cases, the cationic surfactant portion of the cationic surfactant grafted halloysite compound(s) is a cationic surfactant other than cetyltrimethylammonium chloride when the amount of cationic surfactant grafted halloysite compound(s) in the cosmetic composition is 3 wt. % or more, based on the total weight of the cosmetic composition.

The cationic surfactant grafted halloysite compound may have a weight ratio of the cationic surfactant portion to halloysite portion that is about 1:99 to about 15:85. For example, the weight ratio of the cationic surfactant portion to halloysite portion of the cationic surfactant grafted halloysite may be about about 2:98 to about 15:85, about 4:96 to about 15:85, about 6:94 to about 15:85, about 8:92 to about 15:85, about 10:90 to about 15:85; about 2:98 to about 13:87, about 2:98 to about 11:89, about 2:98 to about 10:90, about 2:98 to about 8:92, or about 2:98 to about 6:94. In one instance, the weight ratio of the cationic surfactant portion to halloysite portion of the cationic surfactant grafted halloysite is about 5:95 to about 10:90.

Nonionic Surfactant(s), Cationic Surfactants(s), and Mixtures Thereof

The cosmetic composition include one or more nonionic surfactant(s), cationic surfactant(s), or a mixture thereof. The total amount of nonionic surfactant(s), cationic surfactant(s) or mixtures thereof (excluding the cationic surfactant grafted halloysite compound) present in the cosmetic composition may be about 0.5 to about 10 wt. %, based on the total weight of the cosmetic composition. In some cases, the total amount of nonionic surfactant(s), cationic surfactant(s) or mixtures thereof (excluding the cationic surfactant grafted halloysite compound) is about 0.5 to about 10 wt. %, about 0.5 to about 9 wt. %, about 0.5 to about 8 wt. %, about 0.5 to about 7 wt. %, about 0.5 to about 6 wt. %, about 0.5 to about 5 wt. %, about 0.5 to about 4 wt. %, about 0.5 to about 3 wt. %, about 0.5 to about 2 wt. %; about 0.75 to about 10 wt. %, about 0.75 to about 9 wt. %, about 0.75 to about 8 wt. %, about 0.75 to about 7 wt. %, about 0.75 to about 6 wt. %, about 0.75 to about 5 wt. %, about 0.75 to about 4 wt. %, about 0.75 to about 3 wt. %, about 0.75 to about 2 wt. %; about 1 to about 10 wt. %, about 1 to about 9 wt. %, about 1 to about 8 wt. %, about 1 to about 7 wt. %, about 1 to about 6 wt. %, about 1 to about 5 wt. %, about 1 to about 4 wt. %, about 1 to about 3 wt. %, about 1 to about 2 wt. %; about 1.5 to about 10 wt. %, about 1.5 to about 9 wt. %, about 1.5 to about 8 wt. %, about 1.5 to about 7 wt. %, about 1.5 to about 6 wt. %, about 1.5 to about 5 wt. %, about 1.5 to about 4 wt. %, about 1.5 to about 3 wt. %; about 2 to about 10 wt. %, about 2 to about 9 wt. %, about 2 to about 8 wt. %, about 2 to about 7 wt. %, about 2 to about 6 wt. %, about 2 to about 5 wt. %, about 2 to about 4 wt. %, about 2 to about 3 wt. %, including ranges and subranges therebetween, based on the total weight of the cosmetic composition.

Nonionic Surfactant(s)

The cosmetic composition may comprise one or more nonionic surfactant(s) in one of the aforementioned listed amounts for the total amount of nonionic surfactant(s), cationic surfactant(s) or mixtures thereof, solely or in combination with one or more cationic surfactant(s). When in combination with cationic surfactant(s), the amount of nonionic surfactants present in the cosmetic composition may be less than the aforementioned listed amounts for the total amount of nonionic surfactant(s), cationic surfactant(s), or mixtures thereof. For example, when in combination with cationic surfactant(s), the amount of nonionic surfactants may be about 0.05 to about 9 wt. %, about 0.05 to about 7 wt. %, about 0.05 to about 5 wt. %, about 0.05 to about 4 wt. %, about 0.05 to about 3 wt. %, about 0.05 to about 2 wt. %, about 0.05 to about 1 wt. %; about 0.1 to about 9 wt. %, about 0.1 to about 7 wt. %, about 0.1 to about 5 wt. %, about 0.1 to about 4 wt. %, about 0.1 to about 3 wt. %, about 0.1 to about 2 wt. %, about 0.1 to about 1 wt. %; about 0.25 to about 9 wt. %, about 0.25 to about 7 wt. %, about 0.25 to about 5 wt. %, about 0.25 to about 4 wt. %, about 0.25 to about 3 wt. %, about 0.25 to about 2 wt. %, about 0.25 to about 1 wt. %; about 0.5 to about 9 wt. %, about 0.5 to about 7 wt. %, about 0.5 to about 5 wt. %, about 0.5 to about 4 wt. %, about 0.5 to about 3 wt. %, about 0.5 to about 2 wt. %, or about 0.5 to about 1 wt. %, including ranges and subranges therebetween, based on the total weight of the cosmetic composition.

The one or more nonionic surfactants in the cosmetic composition may be alkanolam ides; alkyl polyglucosides; polyoxyalkylenated nonionic surfactants; polyglycerolated nonionic surfactants; ethoxylated fatty esters, and/or ethoxylated oils from plant origin. Non-limiting examples of nonionic surfactants include: alkanolam ides; alkyl polyglucosides; polyoxyalkylenated nonionic surfactants; polyglycerolated nonionic surfactants; ethoxylated fatty esters; alcohols, alpha-diols, alkylphenols and esters of fatty acids, being ethoxylated, propoxylated or glycerolated; copolymers of ethylene oxide and/or of propylene oxide; condensates of ethylene oxide and/or of propylene oxide with fatty alcohols; polyethoxylated fatty amides; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol $(C_6\text{-}C_{24})$alkylpolyglycosides; N—$(C_6\text{-}C_{24})$alkylglucamine derivatives, amine oxides such as $(C_{10}\text{-}C_{14})$alkylamine oxides or N—$(C_{10}\text{-}C_{14})$acylaminopropylmorpholine oxides; and mixtures thereof. In some cases, the plurality of nonionic surfactants can be useful.

Further discussion of nonionic surfactants that may be suitable in the cosmetic compositions is provided below:

(i) Alkanolamides

Non-limiting examples alkanolam ides include fatty acid alkanolam ides. The fatty acid alkanolamides may be fatty acid monoalkanolamides, fatty acid dialkanolamides, or fatty acid isoalkanolam ides, and may have a $C_{2-8}$ hydroxyalkyl group (the $C_{2-8}$ chain can be substituted with one or more than one —OH group). Non-limiting examples include fatty acid diethanolam ides (DEA) or fatty acid monoethanolam ides (MEA), fatty acid monoisopropanolamides (MIPA), fatty acid diisopropanolamides (DIPA), and fatty acid glucamides (acyl glucamides).

Suitable fatty acid alkanolam ides include those formed by reacting an alkanolamine and a C6-C36 fatty acid. Examples include, but are not limited to: oleic acid diethanolamide, myristic acid monoethanolamide, soya fatty acids diethanolamide, stearic acid ethanolamide, oleic acid monoisopropanolamide, linoleic acid diethanolamide, stearic acid monoethanolamide (Stearamide MEA), behenic acid monoethanolamide, isostearic acid monoisopropanolamide (isostearamide MIPA), erucic acid diethanolamide, ricinoleic acid monoethanolamide, coconut fatty acid monoisopropanolamide (cocoamide MIPA), coconut acid monoethanolamide (Cocamide MEA), palm kernel fatty acid diethanolamide, coconut fatty acid diethanolamide, lauric diethanolamide, polyoxyethylene coconut fatty acid monoethanolamide, coconut fatty acid monoethanolamide, lauric monoethanolamide, lauric acid monoisopropanolamide (lauramide MIPA), myristic acid monoisopropanolamide (Myristamide MIPA), coconut fatty acid diisopropanolamide (cocamide DIPA), and mixtures thereof.

In some instances, the fatty acid alkanolam ides preferably include cocamide MIPA, cocamide DEA, cocamide MEA, cocamide DIPA, and mixtures thereof. In particular, the fatty acid alkanolamide may be cocamide MIPA, which is commercially available under the tradename EMPILAN from Innospec Active Chemicals.

Fatty acid alkanolam ides include those of the following structure:

wherein, $R_4$ is an alkyl chain of 4 to 20 carbon atoms ($R_4$ may be, for example, selected from lauric acid, coconut acid, palmitic acid, myristic acid, behenic acid, babassu fatty acid, isostearic acid, stearic acid, corn fatty acid, soy fatty acid, shea butter fatty acids, caprylic acid, capric acid, and mixtures thereof);

$R_6$ is selected from —$CH_2OH$, —$CH_2CH_2OH$, —$CH_2CH_2CH_2OH$, —$CH_2(CHOH)_4CH_2OH$, -benzyl, and mixtures thereof; and $R_6$ is selected from —H, —$CH_3$, —$CH_2OH$, —$CH_2CH_3$, —$CH_2CH_2OH$, —$CH_2CH_2CH_2OH$, —$CH_2(CHOH)_4CH_2OH$, -benzyl, and mixtures thereof.

In some instances, the one or more of the fatty acid alkanolamides include one or more acyl glucam ides, for example, acyl glucam ides having a carbon chain length of 8 to 20. Non-limiting examples include lauroyl/myristoyl methyl glucamide, capryloyl/capryl methyl glucamide, lauroyl methyl glucamide, myristoyl methyl glucamide, capryloyl methyl glucamide, capryl methyl glucamide, cocoyl methyl glucamide, capryloyl/caproyl methyl glucamide, cocoyl methyl glucamide, lauryl methylglucamide, oleoyl methylglucamide oleate, stearoyl methylglucamide stearate, sunfloweroyl methylglucamide, and tocopheryl succinate methylglucamide.

(ii) Alkyl Polyglucosides

Examples of alkyl polyglucosides include those having the following formula:

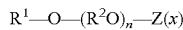

wherein,
$R^1$ is an alkyl group having 8-18 carbon atoms;
$R^2$ is an ethylene or propylene group;
Z is a saccharide group with 5 to 6 carbon atoms;
n is an integer from 0 to 10; and
x is an integer from 1 to 5.

Non-limiting examples of alkyl polyglucosides that may be useful in the cosmetic compositions include lauryl glucoside, octyl glucoside, decyl glucoside, coco glucoside, caprylyl/capryl glucoside, and sodium lauryl glucose carboxylate. Typically, the at least one alkyl poly glucoside compound is selected from the group consisting of lauryl glucoside, decyl glucoside and coco glucoside. In some instances, the nonionic surfactant is decyl glucoside.

(iii) Miscellaneous Nonionic Surfactants

Nonionic surfactants also include, for example, alcohols, alpha-diols, alkylphenols and esters of fatty acids, being ethoxylated, propoxylated or glycerolated and having at least one fatty chain comprising, e.g., from 8 to 18 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, e.g., from 2 to 30 mole of ethylene oxide; polyglycerolated fatty amides comprising, e.g., from 1.5 to 5 glycerol groups, such as from 1.5 to 4; ethoxylated fatty acid esters of sorbitan comprising from 2 to 30 mole of ethylene oxide; ethoxylated oils from plant origin; fatty acid esters of sucrose; fatty acid esters of polyethylene glycol; polyethoxylated fatty acid mono or diesters of glycerol ($C_6$-$C_{24}$)alkylpolyglycosides; N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides; and mixtures thereof. In some instances, the nonionic surfactant is chosen from polyoxyalkylenated or polyglycerolated nonionic surfactants. The oxyalkylene units are more particularly oxyethylene or oxypropylene units, or a combination thereof, and are preferably oxyethylene units.

Additionally or alternatively, the nonionic surfactant may be selected from esters of polyols with fatty acids with a saturated or unsaturated chain containing, e.g., from 8 to 24 carbon atoms, preferably 12 to 22 carbon atoms, and alkoxylated derivatives thereof, preferably with a number of alkyleneoxide of from 10 to 200, and more preferably from 10 to 100, such as glyceryl esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; polyethylene glycol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sorbitol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sugar (sucrose, glucose, alkylglycose) esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; ethers of fatty alcohols; ethers of sugar and a $C_8$-$C_{24}$, preferably $C_{12}$-$C_{22}$, fatty alcohol or alcohols; and mixtures thereof.

Examples of ethoxylated fatty esters that may be mentioned include the adducts of ethylene oxide with esters of lauric acid, palmitic acid, stearic acid or behenic acid, and mixtures thereof, especially those containing from 9 to 100 oxyethylene groups, such as PEG-9 to PEG-50 laurate (as the CTFA names: PEG-9 laurate to PEG-50 laurate); PEG-9 to PEG-50 palm itate (as the CTFA names: PEG-9 palm itate to PEG-50 palmitate); PEG-9 to PEG-50 stearate (as the CTFA names: PEG-9 stearate to PEG-50 stearate); PEG-9 to PEG-50 palm itostearate; PEG-9 to PEG-50 behenate (as the CTFA names: PEG-9 behenate to PEG-50 behenate); polyethylene glycol 100 EO monostearate (CTFA name: PEG-100 stearate); and mixtures thereof.

The nonionic surfactant may be chosen from glyceryl esters of fatty acids, such as glyceryl stearate (glyceryl mono-, di- and/or tristearate) (CTFA name: glyceryl stearate), glyceryl ricinoleate, and mixtures thereof. The glyceryl esters of fatty acids may be glyceryl esters of $C_8$-$C_{24}$ alkoxylated fatty acids and/or polyethoxylated glyceryl stearate (glyceryl mono-, di- and/or tristearate), such as PEG-20 glyceryl stearate.

Cationic Surfactant(s)

The cosmetic composition may comprise one or more cationic surfactant(s) in one of the aforementioned listed amounts for the total amount of nonionic surfactant(s), cationic surfactant(s), or mixtures thereof, singularly or in combination with nonionic surfactant(s). When in combination with nonionic surfactant(s), the amount of cationic surfactant present in the cosmetic composition may be less than the aforementioned listed amounts for the total amount of nonionic surfactant(s), cationic surfactant(s), or mixtures thereof. For example, when in combination with nonionic surfactant(s), the amount of cationic surfactants may be about 0.05 to about 9 wt. %, about 0.05 to about 7 wt. %, about 0.05 to about 5 wt. %, about 0.05 to about 4 wt. %, about 0.05 to about 3 wt. %, about 0.05 to about 2 wt. %, about 0.05 to about 1 wt. %, about 0.05 to about 0.5 wt. %; about 0.1 to about 9 wt. %, about 0.1 to about 7 wt. %, about 0.1 to about 5 wt. %, about 0.1 to about 4 wt. %, about 0.1 to about 3 wt. %, about 0.1 to about 2 wt. %, about 0.1 to about 1 wt. %, about 0.1 to about 0.5 wt. %; about 0.25 to about 9 wt. %, about 0.25 to about 7 wt. %, about 0.25 to about 5 wt. %, about 0.25 to about 4 wt. %, about 0.25 to about 3 wt. %, about 0.25 to about 2 wt. %, about 0.25 to about 1 wt. %; about 0.5 to about 9 wt. %, about 0.5 to about 7 wt. %, about 0.5 to about 5 wt. %, about 0.5 to about 4 wt.

%, about 0.5 to about 3 wt. %, about 0.5 to about 2 wt. %, or about 0.5 to about 1 wt. %, including ranges and subranges therebetween, based on the total weight of the cosmetic composition.

The cosmetic compositions may include one or more cationic surfactants (in addition to the cationic surfactant grafted halloysite compound). For example, the cosmetic composition may include a cationic surfactant chosen from cetrimonium chloride, steartrimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyidiethylamine, arachidamidoethyidimethylamine, and mixtures thereof.

Additional, non-limiting examples of cationic surfactants include behenalkonium chloride, benzethonium chloride, cetylpyridinium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, hexadecyltrimethyl ammonium bromide, and mixtures thereof.

The cationic surfactant(s) may also be chosen from optionally polyoxyalkylenated, primary, secondary or tertiary fatty amines, or salts thereof, and quaternary ammonium salts, and mixtures thereof. In some cases, it is useful to use salts such as chloride salts of the quaternary ammonium compounds. The fatty amines generally comprise at least one $C_8$-$C_{30}$ hydrocarbon-based chain. For example, quaternary ammonium salts, which may be incorporated in certain instances, include those corresponding to the following general formula:

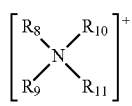

in which the groups $R_8$ to $R_{11}$, which may be identical or different, represent a linear or branched, saturated or unsaturated aliphatic group comprising from 1 to 30 carbon atoms, or an aromatic group such as aryl or alkylaryl, at least one of the groups $R_8$ to $R_{11}$ denoting a group comprising from 8 to 30 carbon atoms and preferably from 12 to 24 carbon atoms. The aliphatic groups may comprise heteroatoms such as oxygen, nitrogen, sulfur and halogens. The aliphatic groups may be chosen, e.g., from $C_1$-$C_{30}$ alkyl, $C_2$-$C_{30}$ alkenyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate and $C_1$-$C_{30}$ hydroxyalkyl groups; $X^-$ is an anion chosen from the group of halides, phosphates, acetates, lactates, ($C_1$-$C_4$)alkyl sulfates, and ($C_1$-$C_4$)alkyl- or ($C_1$-$C_4$) alkylarylsulfonates.

Among the quaternary ammonium salts having a structure in accordance with the above formula, those that may be preferable include, on the one hand, tetraalkylammonium salts (e.g., dialkyldimethylammonium) and alkyltrimethylammonium salts in which the alkyl group contains approximately from 12 to 22 carbon atoms (e.g., behenyltrimethylammonium, distearyldimethylammonium, cetyltrimethylammonium or benzyldimethylstearylammonium salts), or, on the other hand, oleocetyldimethylhydroxyethylammonium salts, palm itylam idopropyltrimethylammonium salts, stearamidopropyltrimethylammonium salts and stearamidopropyldimethylcetearylammonium salts.

Examples of quaternary ammonium salt of imidazoline, which may be incorporated in certain instances, include those having a structure according to the general formula provided below:

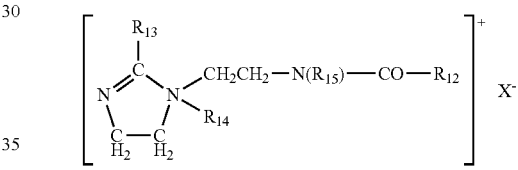

in which $R_{12}$ represents an alkenyl or alkyl group comprising from 8 to 30 carbon atoms, derived for example from tallow fatty acids, $R_{13}$ represents a hydrogen atom, a $C_1$-$C_4$ alkyl group or an alkyl or alkenyl group comprising from 8 to 30 carbon atoms, $R_{14}$ represents a $C_1$-$C_4$ alkyl group, $R_{15}$ represents a hydrogen atom or a $C_1$-$C_4$ alkyl group, $X^-$ is an anion chosen from the group of halides, phosphates, acetates, lactates, alkyl sulfates, alkyl- or alkylarylsulfonates in which the alkyl and aryl groups preferably comprise, respectively, from 1 to 20 carbon atoms and from 6 to 30 carbon atoms. $R_{12}$ and $R_{13}$ preferably denote a mixture of alkenyl or alkyl groups containing from 12 to 21 carbon atoms, derived for example from tallow fatty acids, $R_{14}$ preferably denotes a methyl group, and $R_{15}$ preferably denotes a hydrogen atom.

Examples of quaternary diammonium or triammonium salt, which may be incorporated in certain instances, include those having a structure in accordance with the following general formula:

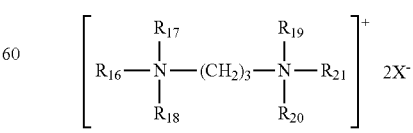

in which $R_{16}$ denotes an alkyl radical comprising approximately from 16 to 30 carbon atoms, which is optionally hydroxylated and/or interrupted with one or more oxygen atoms; $R_{17}$ is chosen from hydrogen or an alkyl radical comprising from 1 to 4 carbon atoms or a group $(R_{16a})(R_{17a})(R_{18a})N-(CH_2)_3$, $R_{16a}$, $R_{17a}$, $R_{18a}$, $R_{18}$, $R_{19}$, $R_{20}$ and $R_{21}$, which may be identical or different, being chosen from hydrogen and an alkyl radical comprising from 1 to 4 carbon atoms; and $X^-$ is an anion chosen from the group of halides, acetates, phosphates, nitrates and methyl sulfates. Such compounds are, for example, Finquat CT-P, sold by the company Finetex (Quaternium 89), and Finquat CT, sold by the company Finetex (Quaternium 75), Examples of cationic/cationizable surfactants, which may be incorporated in certain instances, include those having a structure in accordance with the general formula provided below:

R4-A-R5-B wherein R4 is a saturated or unsaturated, straight or branched alkyl chain with 8 to 24 C atoms, R5 is a straight or branched alkyl chain with 1 to 4 C atoms, A is selected from:

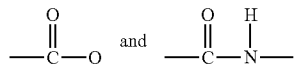

and B is selected from:

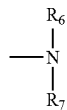

wherein $R_6$ and $R_7$ are the same or different and are H or an alkyl chain with 1 to 4 C atoms, hydroxyl alkyl chain with 1 to 4 C atoms and di hydroxyl alkyl chain with 2 to 4 C atoms;

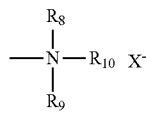

$R_8$ and $R_9$, which may be the same or different, are an alkyl chain with 1 to 4 C atoms, hydroxyl alkyl chain with 1 to 4 C atoms and di hydroxyl alkyl chain with 2 to 4 C atoms; and $R_{10}$ is an alkyl chain with 1 to 4 C atoms, hydroxyl alkyl chain with 1 to 4 C atoms or di hydroxyl alkyl chain with 2 to 4 C atoms.

In some instances, $R_4$ is saturated or unsaturated, straight or branched alkyl chain with 10 to 24 C atoms, more preferably 12 to 22 C atoms and $R_5$ is straight or branched alkyl group with 1 to 4 C atoms, and A, B, $R_6$ to $R_{10}$ are same as above.

Non-limiting suitable examples are stearyloxypropyl amine, palmityloxypropyl amine, stearyloxypropyldimethyl amine, stearyloxypropyldiethyl amine, stearyloxyethylyldimethyl amine, stearyloxyethyl amine, myristyloxypropyl amine, myristyloxypropyldimethyl amine, palm itam idopropyl amine, palm itam idopropyl methylamine, palm itam idopropyl diethylamine, palm itam idopropyl dibutylamine, palm itam idopropyl buylamine, palm itam idopropyl dipropylamine, palm itam idopropyl propylamine, palm itam idopropyl dihydroxyethylamine, palm itam idopropyl hydroxyethylamine, palm itam idopropyl dihydroxypropylamine, palm itam idopropyl hydroxypropylamine, lauramidopropyl amine, lauramidopropyl methylamine, lauramidopropyl diethylamine, lauramidopropyl dibutylamine, lauramidopropyl buylamine, lauramidopropyl dipropylamine, lauramidopropyl propylamine, lauramidopropyl dihydroxyethylamine, lauramidopropyl hydroxyethylamine, lauramidopropyl dihydroxypropylamine, lauramidopropyl hydroxypropylamine, stearamidopropyl amine, stearamidopropyl dimethylamine, steara midopropyl diethylamine, stearamidopropyldibutylamine, stearamidopropyl butylamine, stearamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, behenamidopropyl amine, behenamidopropyl methylamine, behenamidopropyl diethylamine, behenamidopropyl dibutylamine, behenamidopropyl butylamine, behenamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, dipalmitamidopropyl methylamine, dipalmitamidopropyl ethylamine, dipalmitamidopropyl butylamine, dipalmitamidopropyl propylamine, dipalmitamidopropyl hydroxyethylamine, dipalmitamidopropyl hydroxypropylamine, dilauramidopropyl amine, dilauramidopropyl methylamine, dilauramidopropyl buylamine, dilauramidopropyl hydroxyethylamine, dilauramidopropyl hydroxypropylamine, distearamidopropyl amine, distearamidopropyl methylamine, dibehenamidopropyl propylamine, dibehenamidopropyl hydroxyethylamine, palm itoam idopropyl trimethyl ammonium chloride, stearamidopropyl trimethylammonium chloride, behenamidopropyl tri hydroxyethalmonium chloride, distearylamidopropyl dimethyl ammonium chloride, dicetylamidodihydroxyethyl ammonium chloride, palm itoylpropyl amine, palm itoylpropyl methylamine, palm itoylpropyl diethylamine, palm itoylpropyl dibutylamine, palm itoylpropyl buylamine, palm itoylpropyl dipropylamine, palm itoylpropyl propylamine, palm itoylpropyl dihydroxyethylamine, palm itoylpropyl hydroxyethylamine, palm itoylpropyl dihydroxypropylamine, palm itoylpropyl hydroxypropylamine, myristoylpropyl amine, myristoylpropyl methylamine, myristoylpropyl diethylamine, myristoylpropyl dibutylamine, myristoylpropyl buylamine, myristoylpropyl dipropylamine, myristoylpropyl propylamine, myristoylpropyl dihydroxyethylamine, myristoylpropyl hydroxyethylamine, myristoylpropyl dihydroxypropylamine, myristoylpropyl hydroxypropylamine, stearoylpropyl amine, stearoylpropyl methylamine, stearoylpropyl diethylamine, stearoylpropyl dibutylamine, stearoylpropyl butylamine, stearoylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, behenylpropyl amine, behenylpropyl methylamine, behenylpropyl diethylamine, behenylpropyl dibutylamine, behenylpropyl butylamine, behenylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, dipalmitoylpropyl methylamine, dipalmitoylpropyl ethylamine, dipalmitylpropyl butylamine, dipalmitylpropyl propylamine, dipalmitylpropyl hydroxyethylamine, dipalmitylpropyl hydroxypropylamine, dilauroylpropyl amine, dilauroylpropyl methylamine, dilauroylpropyl buylamine, dilauroylpropyl hydroxyethylamine, dilauroylpropyl hydroxypropylamine, distearylpropyl amine, distearylpropyl methylamine, dibehenylpropyl propylamine, dibehenylpropyl hydroxyethylamine, palm itylpropyl trimethyl ammonium chloride, stearylpropyl trimethylammonium chloride, behenylpropyl tri hydroxyethalmonium chloride, distearylpropyl dimethyl ammonium chloride, dicetyldihydroxyethyl ammonium chloride, dioleoylethylhydroxyethylmonium methosulfate, and dicocoylethylhydroxyethylmonium methosulfate.

Cationizable surfactants may be chosen from fatty alkylamines, preferably, fatty dialkylamines. Non-limiting examples include dimethyl lauramine, dimethyl behenamine, dimethyl cocamine, dimethyl myristamine, dimethyl palm itam ine, dimethyl stearamine, dimethyl tallowamine, dimethyl soyamine, and mixtures thereof. Fatty dialkylamines include fatty amidoamine compounds, their salts, and mixtures thereof. Non-limiting examples of fatty dialkylamines include oleamidopropyl dimethylamine, linoleamidopropyl dimethylamine, isostearamidopropyl dimethylamine, stearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, and palm itam idopropyl dimethylamine.

Non-polymeric, mono-, di-, and/or tri-carboxylic acids may be used to "neutralize" the fatty dialkylamines. In some cases, the one or more non-polymeric, mono-, di-, and/or tri-carboxylic acids include at least one dicarboxylic acid. Non-limiting examples include lactic acid, oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, benzoic acid, and mixtures thereof. In particular, lactic acid or tartaric acid or mixtures thereof are useful, especially in combination with fatty dimethylamines such as, e.g., stearamidopropyl dimethylamine.

The cosmetic composition may be formulated such that the two or more cationic surfactants are associated with the same or different balancing anionic ions. For example, at least one of the two or more cationic surfactants may have a chloride ion and/or a sulfate ion. In some instances, the two or more cationic surfactants comprise cetrimonium chloride and one or both of behentrimonium methosulfate and behentrimonium chloride. In further instances, the two or more cationic surfactants comprise behentrimonium chloride and one or both of behentrimonium methosulfate and cetrimonium chloride.

In some embodiments, cosmetic composition may be formulated with a cationic surfactant chosen from behentrimonium chloride, cetrimonium chloride, behentrimonium methosulfate, or mixtures thereof. In yet further embodiments, the cationic surfactant(s) is chosen from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, stearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamidopropyidiethylamine, arachidamidoethyidiethylamine, arachidamidoethyidimethylamine, and a mixture thereof.

Amphoteric Surfactant(s)

The cosmetic composition may comprise amphoteric surfactant(s), e.g., in an amount of about 0.05 to about 10 wt. %, based on the total weight of the cosmetic composition. In some cases, the amount of amphoteric surfactant(s) present in the cosmetic composition is about 0.05 to about 10 wt. %, about 0.05 to about 9 wt. %, about 0.05 to about 8 wt. %, about 0.05 to about 7 wt. %, about 0.05 to about 6 wt. %, about 0.05 to about 5 wt. %, about 0.05 to about 4 wt. %, about 0.05 to about 3 wt. %, about 0.05 to about 2 wt. %, 0.05 to about 1 wt. %; about 0.1 to about 10 wt. %, about 0.1 to about 9 wt. %, about 0.1 to about 7 wt. %, about 0.1 to about 5 wt. %, about 0.1 to about 4 wt. %, about 0.1 to about 3 wt. %, about 0.1 to about 2 wt. %, about 0.1 to about 1 wt. %; about 0.25 to about 10 wt. %, about 0.25 to about 9 wt. %, about 0.25 to about 7 wt. %, about 0.25 to about 5 wt. %, about 0.25 to about 4 wt. %, about 0.25 to about 3 wt. %, about 0.25 to about 2 wt. %, about 0.25 to about 1 wt. %; about 0.5 to about 10 wt. %, about 0.5 to about 9 wt. %, about 0.5 to about 7 wt. %, about 0.5 to about 5 wt. %, about 0.5 to about 4 wt. %, about 0.5 to about 3 wt. %, about 0.5 to about 2 wt. %, about 0.5 to about 1 wt. %; about 0.75 to about 10 wt. %, about 0.75 to about 9 wt. %, about 0.75 to about 8 wt. %, about 0.75 to about 7 wt. %, about 0.75 to about 6 wt. %, about 0.75 to about 5 wt. %, about 0.75 to about 4 wt. %, about 0.75 to about 3 wt. %, about 0.75 to about 2 wt. %; about 1 to about 10 wt. %, about 1 to about 9 wt. %, about 1 to about 8 wt. %, about 1 to about 7 wt. %, about 1 to about 6 wt. %, about 1 to about 5 wt. %, about 1 to about 4 wt. %, about 1 to about 3 wt. %, about 1 to about 2 wt. %; about 1.5 to about 10 wt. %, about 1.5 to about 9 wt. %, about 1.5 to about 8 wt. %, about 1.5 to about 7 wt. %, about 1.5 to about 6 wt. %, about 1.5 to about 5 wt. %, about 1.5 to about 4 wt. %, about 1.5 to about 3 wt. %; about 2 to about 10 wt. %, about 2 to about 9 wt. %, about 2 to about 8 wt. %, about 2 to about 7 wt. %, about 2 to about 6 wt. %, about 2 to about 5 wt. %, about 2 to about 4 wt. %, about 2 to about 3 wt. %, including ranges and subranges therebetween, based on the total weight of the cosmetic composition.

The cosmetic composition may include amphoteric surfactants such as, e.g., alkyl amphoprionates, betaines, alkyl sultaines, alkyl amphoacetates, and mixtures thereof. In some instances, it is preferable to include one or more alkyl amphoacetates. Further discussion of amphoteric surfactants that may be included in the cosmetic composition is provide below.

(i) Alkyl Amphopropionates

In some instances, the cosmetic compositions include one or more alkyl amphopropionates. Non-limiting examples of alkyl amphopropionates include cocoamphopropionate, cornamphopropionate, caprylamphopropionate, cornamphopropionate, caproamphopropionate, oleoamphopropionate, isostearoamphopropionate, stearoamphopropionate, lauroamphopropionate, salts thereof, and a mixture thereof. Sodium cocoamphopropionate may be included in the cosmetic composition in some cases.

(ii) Betaines

The amphoteric surfacants may be selected from betaines, such as those having a structure according to the following formulae:

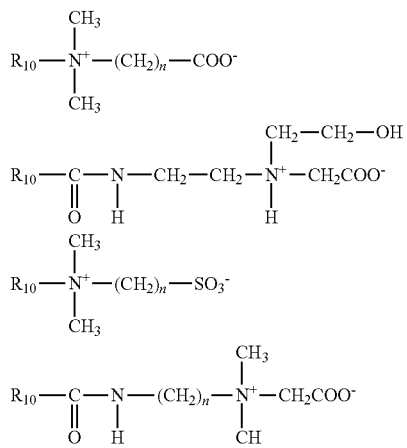

wherein $R_{10}$ is an alkyl group having 8-18 carbon atoms; and n is an integer from 1 to 3.

Examples of betaines include coca betaine, cocamidopropyl betaine, lauryl betaine, laurylhydroxy sulfobetaine, lauryldimethyl betaine, cocamidopropyl hydroxysultaine, behenyl betaine, capryl/capramidopropyl betaine, lauryl hydroxysultaine, stearyl betaine, and mixtures thereof. In some cases, at least one betaine compound is selected from coco betaine, cocamidopropyl betaine, behenyl betaine, capryl/capramidopropyl betaine, and lauryl betaine, and mixtures thereof. In further cases, two or more betaines are included in the cosmetic composition. For example, the cosmetic composition may include coco betaine and cocamidopropyl betaine.

(iii) Alkyl Sultaines

Non-limiting examples of alkyl sultaines include hydroxyl sultaines of the following formula:

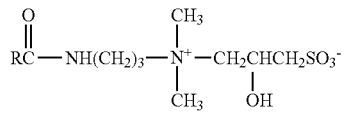

wherein R is an alkyl group having 8-18 carbon atoms. More specific examples include, but are not limited to cocamidopropyl hydroxysultaine, lauryl hydroxysultaine, and a mixture thereof.

(iv) Alkyl Amphoacetates and Alkyl Amphodiacetates

The amphoteric surfactants may be chosen from alkyl amphoacetates and alkyl amphodiacetates, such as those of the following Formulae:

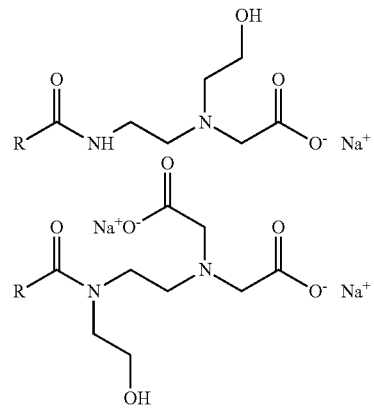

wherein R is an alkyl group having 8-18 carbon atoms. Although sodium is shown as the cation in the above formulae, the cation may be an alkali metal ion such as potassium ions, ammonium ions, or alkanolammonium ions (e.g., monoethanolammonium or triethanolammonium ions). A non-limiting example is sodium lauroamphoacetate.

Additional non-limiting examples of alkyl amphoacetates and alkyl amphodiacetates include those of the following formula:

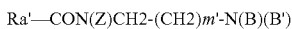

Ra'—CON(Z)CH2-(CH2)m'-N(B)(B')

wherein:
B represents —CH2CH2OX', with X' representing —CH2-COOH, CH2-COOZ', —CH2CH2-COOH, —CH2CH2-COOZ', or a hydrogen atom;
B' represents —CH2)z-Y', with z=1 or 2, and Y' representing —COOH, —COOZ', —CH2-CHOH—SO3H or —CH2-CHOH—SO3Z';
m' is equal to 0, 1 or 2;
Z represents a hydrogen atom or a hydroxyethyl or carboxymethyl group;
Z' represents an ion resulting from an alkali or alkaline-earth metal, such as sodium, potassium or magnesium; an ammonium ion; or an ion resulting from an organic amine and in particular from an amino alcohol, such as monoethanolamine, diethanolamine and triethanolamine, monoisopropanolamine, diisopropanolamine or triisopropanolamine, 2-amino-2-methyl-1-propanol, 2-amino-2-methyl-1,3-propanediol and tris (hydroxy-methyl)aminomethane; and
Ra' represents a (C10-C30)alkyl or alkenyl group of an acid Ra'COOH preferably present in hydrolyzed linseed oil or coconut oil, an alkyl group, in particular a C17 alkyl group, and its iso form, or an unsaturated C17 group.

Exemplary compounds of formula (Ic) include (C8-C20) alkylamphoacetates and (C8-C20)alkylamphodiacetates, such as disodium cocoamphodiacetate, disodium lauroamphodiacetate, disodium caprylamphodiacetate, disodium caprylamphodiacetate, disodium cocoamphodipropionate, disodium lauroamphodipropionate, disodium caprylamphodipropionate, disodium caprylomphodipropionate, lauroamphodipropionic acid, or cocoamphodipropionic acid. For example, disodium cocoamphodiacetate supplied by Rhodia under the name MIRANOLI $C_2M$ can be used.

Polyol(s)

The cosmetic composition may include one or more polyols. The total amount of polyols in the cosmetic composition may vary from, e.g., about 0.1 to about 20 wt. %, based on the total weight of the cosmetic composition. For instance, the total amount of polyols in the cosmetic composition may be about 0.1 to about 20 wt. %, about 0.1 to about 15 wt. %, about 0.1 to about 10 wt. %, about 0.1 to about 8 wt. %, about 0.1 to about 6 wt. %, about 0.1 to about 5 wt. %, about 0.1 to about 4 wt. %, about 0.1 to about 3 wt. %; about 0.5 to about 20 wt. %, about 0.5 to about 15 wt. %, about 0.5 to about 10 wt. %, about 0.5 to about 8 wt. %, about 0.5 to about 6 wt. %, about 0.5 to about 5 wt. %, about 0.5 to about 4 wt. %, about 0.5 to about 3 wt. %; about 1 to about 20 wt. %, about 1 to about 15 wt. %, about 1 to about 10 wt. %, about 1 to about 8 wt. %, about 1 to about 6 wt. %, about 1 to about 5 wt. %, about 1 to about 4 wt. %, about 1 to about 3 wt. %; about 1.5 to about 20 wt. %, about 1.5 to about 15 wt. %, about 1.5 to about 10 wt. %, about 1.5 to about 8 wt. %, about 1.5 to about 6 wt. %, about 1.5 to about 5 wt. %, about 1.5 to about 4 wt. %, about 1.5 to about 3 wt. %; about 2 to about 20 wt. %, about 2 to about 15 wt. %, about 2 to about 10 wt. %, about 2 to about 8 wt. %, about 2 to about 6 wt. %, about 2 to about 5 wt. %, about 2 to about 4 wt. %, about 2 to about 3 wt. %; about 2.5 to about 20 wt. %, about 2.5 to about 15 wt. %, about 2.5 to about 10 wt. %, about 2.5 to about 8 wt. %, about 2.5 to about 6 wt. %, about 2.5 to about 5 wt. %, about 2.5 to about 4 wt. %; about 3 to about 20 wt. %, about 3 to about 15 wt. %, about 3 to about 10 wt. %, about 3 to about 8 wt. %, about 3 to about 6 wt. %, about 3 to about 5 wt. %, about 3 to about 4 wt. %, including ranges and subranges therebetween, based on the total weight of the cosmetic composition.

The polyols of the cosmetic composition may comprise or be chosen from polyols having from 2 to 15 carbon atoms and at least two hydroxyl groups. Exemplary polyols that may be used in the cosmetic composition include and/or may be chosen from alkanediols such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, caprylyl glycol, 1,2-hexanediol, 1,2-pentanediol, and 4-methyl-1,2-pentanediol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; sorbitol; sorbitan; triacetin; and a mixture thereof.

The polyol(s) may be glycols or glycol ethers such as, e.g., monomethyl, monoethyl and monobutyl ethers of ethylene glycol, propylene glycol or ethers thereof such as, e.g., monomethyl ether of propylene glycol, butylene glycol, pentylene glycol, hexylene glycol, dipropylene glycol as well as alkyl ethers of diethylene glycol, e.g., monoethyl ether or monobutyl ether of diethylene glycol. In one instance, the one or more polyols include or are chosen from ethylene glycol, propylene glycol, butylene glycol, pentylene glycol, hexylene glycol, pentylene glycol, 1,3-propanediol, diethylene glycol, dipropylene glycol, caprylyl glycol, glycerin, and a mixture thereof. In another instance, the cosmetic composition includes or is chosen from caprylyl glycol, glycerin, and a mixture thereof.

Fatty Compound(s)

The cosmetic composition may, in some cases, include one or more fatty compound(s), e.g., in an amount of about 0.01 to about 20 wt. %, based on the total weight of the cosmetic composition. In some instances, the amount of fatty compounds present in the cosmetic composition is about 0.1 to 20 wt. %, about 0.1 to about 18 wt. %, about 0.1 to about 16 wt. %, about 0.1 to about 14 wt. %, about 0.1 to about 12 wt. %, about 0.1 to about 10 wt. %, about 0.1 to about 8 wt. %, about 0.1 to about 7 wt. %, about 0.1 to about 6 wt. %, about 0.1 to about 5 wt. %; about 0.5 to 20 wt. %, about 0.5 to about 18 wt. %, about 0.5 to about 16 wt. %, about 0.5 to about 14 wt. %, about 0.5 to about 12 wt. %, about 0.5 to about 10 wt. %, about 0.5 to about 8 wt. %, about 0.5 to about 7 wt. %, about 0.5 to about 6 wt. %, about 0.5 to about 5 wt. %; about 1 to about 20 wt. %, about 1 to about 18 wt. %, about 1 to about 16 wt. %, about 1 to about 14 wt. %, about 1 to about 12 wt. %, about 1 to about 10 wt. %, about 1 to about 8 wt. %, about 1 to about 7 wt. %, about 1 to about 6 wt. %, about 1 to about 5 wt. %; about 2 to about 20 wt. %, about 2 to about 18 wt. %, about 2 to about 16 wt. %, about 2 to about 14 wt. %, about 2 to about 12 wt. %, about 2 to about 10 wt. %, about 2 to about 8 wt. %, about 2 to about 7 wt. %, about 2 to about 6 wt. %, about 2 to about 5 wt. %; about 3 to about 20 wt. %, about 3 to about 18 wt. %, about 3 to about 16 wt. %, about 3 to about 14 wt. %, about 3 to about 12 wt. %, about 3 to about 10 wt. %, about 3 to about 8 wt. %, about 3 to about 7 wt. %, about 3 to about 6 wt. %, about 3 to about 5 wt. %; about 4 to about 20 wt. %, about 4 to about 18 wt. %, about 4 to about 16 wt. %, about 4 to about 14 wt. %, about 4 to about 12 wt. %, about 4 to about 10 wt. %, about 4 to about 8 wt. % about 4 to about 7 wt. %, about 4 to about 6 wt. %, about 4 to about 5 wt. %; about 5 to about 20 wt. %, about 5 to about 18 wt. %, about 5 to about 16 wt. %, about 5 to about 14 wt. %, about 5 to about 12 wt. %, about 5 to about 10 wt. %, or about 5 to about 8 wt. %, about 5 to about 7 wt. %, or about 5 to about 6 wt. %, including all ranges and sub-ranges therebetween, based on the total weight of the cosmetic composition.

Examples of fatty compound(s) that may be incorporated into the cosmetic composition include fatty alcohol, a fatty ester, a fatty ether, a fatty acid, a derivative thereof, or a mixture thereof. Additional examples of fatty compounds that are worth mentioning include oils, mineral oil, alkanes (paraffins), fatty alcohol derivatives, fatty acid derivatives, esters of fatty alcohols, hydroxy-substituted fatty acids, waxes, triglyceride compounds, lanolin, and a mixture thereof. Further examples of fatty compounds are discussed below.

Fatty Ester(s)

The cosmetic compositions may include one or more fatty compound(s) that is a fatty ester. For example, the fatty compound(s) may be chosen from from dialkyl carbonates of formula: $R_1O(C=O)R_2$, wherein $R_1$ and $R_2$ are independently linear or branched, saturated or unsaturated alkyl chains having 1 to 30 carbon atoms, or having 2 to 28 carbon atoms, or having 4 to 25 carbon atoms, or having 6 to 22 carbon atoms, preferably one or more fatty carbonates selected from C14-15 dialkyl carbonate, dicaprylyl carbonate, diethyl carbonate, dihexyl carbonate, diethylhexyl carbonate, dimethoxyphenyl phenyloxoethyl ethylcarbonate, dimethyl carbonate, dipropyl carbonate, dipropylheptyl carbonate, dioctyl carbonate, and a mixture thereof.

Additionally or alternatively, the fatty ester chosen from cetyl ester, purcellin oil (cetearyl octanoate), isopropyl myristate, isopropyl palmitate, $C_{12}$-$C_{15}$ alkyl benzoate, 2-ethylphenyl benzoate, isopropyl lanolate, hexyl laurate, diisopropyl adipate, isononyl isononanoate, oleyl erucate, 2-ethylhexyl palmitate, isostearyl isostearate, diisopropyl sebacate, octanoates, decanoates or ricinoleates of alcohols or polyalcohols, hydroxylated esters, dicaprylyl carbonate, pentaerythritol esters, and a mixture thereof. Other fatty esters worth mentioning include polyglyceryl-10 oleate, polyglyceryl-10 dioleate, polyglyceryl-6 stearate, polyglyceryl-6 distearate, polyglyceryl-10 stearate, polyglyceryl-10 distearate, polyglyceryl-8 dipalmitate, polyglyceryl-10 dipalmitate, polyglyceryl-10 behenate, and polyglyceryl-12 trilaurate.

Fatty Alcohol(s)

Suitable fatty alcohols, if present, include those having a fatty group with a carbon chain of greater than 8 carbon atoms, 8 to 50 carbon atoms, 8 to 40 carbon atoms, 8 to 30 carbon atoms, 8 to 22 carbon atoms, 12 to 22 carbon atoms, or 12 to 18 carbon atoms, including all ranges and subranges therebetween. In some instances, the fatty group of the fatty alcohols has a carbon chain of 10 to 20 carbon atoms or 10 to 18 carbon atoms. The fatty alcohols may be chosen from polyethylene glycol ethers, such as those having a fatty alcohol group with a carbon chain of 12 to 16 or 12 to 14 carbon atoms.

The fatty alcohol portion is preferably hydrogenated (for example, stearyl, lauryl, cetyl, cetearyl); however, the fatty alcohol may contain one or more double bonds (for example, oleyl). Non-limiting examples of fatty alcohols include decyl alcohol, undecyl alcohol, dodecyl alcohol, myristyl alcohol, lauryl alcohol, cetyl alcohol, stearyl alcohol, cetearyl alcohol (cetyl alcohol and stearyl alcohol), isostearyl alcohol, isocetyl alcohol, behenyl alcohol, linalool, oleyl alcohol, cis-4-t-butylcyclohexanol, isotridecyl alcohol, myricyl alcohol, and a mixture thereof. In some cases, the fatty alcohols comprise at least one of or may be chosen from myristyl alcohol, lauryl alcohol, cetyl alcohol, stearyl alcohol, cetearyl alcohol, isostearyl alcohol, oleyl alcohol, isotridecyl alcohol, and a mixture thereof.

The fatty alcohol may be saturated or unsaturated. Exemplary saturated liquid fatty alcohols may be branched and optionally contain in their structure at least one aromatic or non-aromatic ring. In some instances, however, the fatty alcohols are acyclic. Non-limiting examples of liquid saturated fatty alcohols include octyldodecanol, isostearyl alcohol, and 2-hexyldecanol.

Exemplary unsaturated liquid fatty alcohol may include in their structure at least one double or triple bond. For example, the fatty alcohols may include several double bonds (such as 2 or 3 double bond), which may be conjugated or non-conjugated. The unsaturated fatty alcohols can be linear or branched and may be acyclic or include in their structure at least one aromatic or non-aromatic ring. Liquid unsaturated fatty alcohols may include or be chosen from oleyl alcohol, linoleyl alcohol, linolenyl alcohol and undecylenyl alcohol.

The fatty alcohols may be alkoxylated fatty alcohols, e.g., having about 1 to about 100 moles of an alkylene oxide per mole of alkoxylated fatty alcohol. For example, the alkoxylated fatty alcohols may be alkoxylated with about 1 to about 80 moles, about 2 to about 50, about 5 to about 45 moles, about 10 to about 40 moles, or 15 to about 35 mores, including all ranges and subranges therebetween, of an alkylene oxide per mole of alkoxylated fatty alcohol.

As examples of alkoxylated fatty alcohols, steareth (for example, steareth-2, steareth-20, and steareth-21), laureth (for example, laureth-4, and laureth-12), ceteth (for example, ceteth-10 and ceteth-20) and ceteareth (for example, ceteareth-2, ceteareth-10, and ceteareth-20) are mentioned. In at least one instance, the one or more alkoxylated fatty alcohols include steareth-20. In some instances, the one or more alkoxylated fatty alcohols may be exclusively steareth-20.

Additional fatty alcohol derivatives that may, optionally be suitable include methyl stearyl ether; 2-ethylhexyl dodecyl ether; stearyl acetate; cetyl propionate; the ceteth series of compounds, such as ceteth-1 through ceteth-45, which are ethylene glycol ethers of cetyl alcochol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof.

Fatty Ether(s)

The fatty compounds may be chosen from fatty ethers. For example, the cosmetic composition may include olyoxyethylene cetyl/stearyl ether, polyoxyethylene cholesterol ether, polyoxyethylene laurate or dilaurate, polyoxyethylene stearate or distearate, polyoxyethylene lauryl or stearyl ether, dicaprylyl ether, dicetyl ether distearyl ether, or a mixture thereof. Non-limiting examples of suitable polyoxyethylene fatty ethers include, but are not limited to, polyoxyethylene cetyl/stearyl ether, polyoxyethylene cholesterol ether, polyoxyethylene laurate or dilaurate, polyoxyethylene stearate or distearate, polyoxyethylene lauryl or stearyl ether, and mixtures thereof, wherein the polyoxyethylene head group ranges from about 2 to about 100 groups. In certain embodiments, the polyoxyethylene fatty ethers include polyoxyethylene stearyl ether, polyoxyethylene myristyl ether, polyoxyethylene lauryl ether having from about 3 to about 10 oxyethylene units and mixtures thereof.

Fatty Acid(s)

In some instances, the fatty compounds may be chosen from fatty acids, fatty acid derivatives, esters of fatty acids, hydroxyl-substituted fatty acids, and alkoxylated fatty acids. The fatty acids may be straight or branched chain acids and/or may be saturated or unsaturated. Non-limiting examples of fatty acids include diacids, triacids, and other multiple acids as well as salts of these fatty acids. For example, the fatty acid may optionally include or be chosen from lauric acid, palmitic acid, stearic acid, behenic acid, arichidonic acid, oleic acid, isostearic acid, sebacic acid, and a mixture thereof. In some cases, the fatty acids are selected from the group consisting of palm itic acid, stearic acid, and a mixture thereof.

Non-limiting examples of polyglycerol esters of fatty acids include those of the following formula:

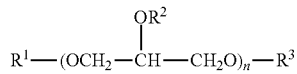

wherein the average value of n is about 3 and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$.

The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substituted fatty acids, and a mixture thereof. Non-limiting examples of fatty acid derivatives include ricinoleic acid, glycerol monostearate, 12-hydroxy stearic acid, ethyl stearate, cetyl stearate, cetyl palm itate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof. Preferred for use herein are glycerol monostearate, 12-hydroxy stearic acid, and a mixture thereof.

Thickening Agent(s)

The cosmetic compositions described herein may, optionally, include a thickening agent. The amount of thickening agents can vary but is typically from about 0.01 to about 20 wt. %, based on the total weight of the cosmetic composition. In some instances, the amount of fatty compounds present in the cosmetic compositions is about 0.1 to 20 wt. %, about 0.1 to about 18 wt. %, about 0.1 to about 16 wt. %, about 0.1 to about 14 wt. %, about 0.1 to about 12 wt. %, about 0.1 to about 10 wt. %, about 0.1 to about 8 wt. %, about 0.1 to about 7 wt. %, about 0.1 to about 6 wt. %, about 0.1 to about 5 wt. %; about 0.5 to 20 wt. %, about 0.5 to about 18 wt. %, about 0.5 to about 16 wt. %, about 0.5 to about 14 wt. %, about 0.5 to about 12 wt. %, about 0.5 to about 10 wt. %, about 0.5 to about 8 wt. %, about 0.5 to about 7 wt. %, about 0.5 to about 6 wt. %, about 0.5 to about 5 wt. %; about 1 to about 20 wt. %, about 1 to about 18 wt. %, about 1 to about 16 wt. %, about 1 to about 14 wt. %, about 1 to about 12 wt. %, about 1 to about 10 wt. %, about 1 to about 8 wt. %, about 1 to about 7 wt. %, about 1 to about 6 wt. %, about 1 to about 5 wt. %; about 2 to about 20 wt. %, about 2 to about 18 wt. %, about 2 to about 16 wt. %, about 2 to about 14 wt. %, about 2 to about 12 wt. %, about 2 to about 10 wt. %, about 2 to about 8 wt. %, about 2 to about 7 wt. %, about 2 to about 6 wt. %, about 2 to about 5 wt. %; about 3 to about 20 wt. %, about 3 to about 18 wt. %, about 3 to about 16 wt. %, about 3 to about 14 wt. %, about 3 to about 12 wt. %, about 3 to about 10 wt. %, about 3 to about 8 wt. %, about 3 to about 7 wt. %, about 3 to about 6 wt. %, about 3 to about 5 wt. %; about 4 to about 20 wt. %, about 4 to about 18 wt. %, about 4 to about 16 wt. %, about 4 to about 14 wt. %, about 4 to about 12 wt. %, about 4 to about 10 wt. %, about 4 to about 8 wt. % about 4 to about 7 wt. %, about 4 to about 6 wt. %, about 4 to about 5 wt. %; about 5 to about 20 wt. %, about 5 to about 18 wt. %, about 5 to about 16 wt. %, about 5 to about 14 wt. %, about 5 to about 12 wt. %, about 5 to about 10 wt. %, or about 5 to about 8 wt. %, about 5 to about 7 wt. %, or about 5 to about 6 wt. %, including all ranges and sub-ranges therebetween, based on the total weight of the cosmetic composition.

The thickening agent(s) may be chosen from xanthan gum, guar gum, biosaccharide gum, cellulose, acacia seneca gum, sclerotium gum, agarose, pechtin, gellan gum, hyaluronic acid. Additionally, the one or more thickening agents may include polymeric thickening agents selected from the group consisting of ammonium polyacryloyldimethyl taurate, ammonium acryloyldimethyltaurate/VP copolymer, sodium polyacrylate, acrylates copolymers, polyacrylamide, carbomer, and acrylates/C10-30 alkyl acrylate crosspolymer. In some cases, the cosmetic composition includes ammonium polyacryloyldimethyl taurate and/or sodium polyacrylate. Suitable thickening agents may be found in U.S. patent application Ser. No. 16/731,654, which is incorporated herein, in its entirety for all purposes.

Many thickening agents are water-soluble, and increase the viscosity of water or form an aqueous gel when the cosmetic composition of the invention is dispersed/dissolved in water. The aqueous solution may be heated and cooled, or neutralized, for forming the gel, if necessary. The thickener may be dispersed/dissolved in an aqueous solvent that is soluble in water, e.g., ethyl alcohol when it is dispersed/dissolved in water.

Particular types of thickening agents that may be mentioned include the following:

One or more thickening agents can optionally be included in the cosmetic compositions of the instant disclosure. Thickening agents may be referred to as "thickeners" or "viscosity modifying agents." Thickening agents are typically included to increase the viscosity of the cosmetic compositions. Nonetheless, in some instances, certain thickening agents provide additional, surprising benefits to the cosmetic compositions. Non-limiting examples of thickening agents include polyacrylate crosspolymers or cross-linked polyacrylate polymers, cationic acrylate copolymers, anionic acrylic or carboxylic acid polymers, polyacrylamide polymers, polysaccharides such as cellulose derivatives, gums, polyquaterniums, vinylpyrrolidone homopolymers/copolymers, C8-24 hydroxyl substituted aliphatic acid, C8-24 conjugated aliphatic acid, sugar fatty esters, polyglyceryl esters, and a mixture thereof. Particular types of thickening agents that may be mentioned include the following:

Carboxylic Acid or Carboxylate Based
Homopolymer or Co-Polymer, Which Can Be
Linear or Crosslinked These polymers contain one or more monomers derived from acrylic acid, substituted acrylic acids, and salts and esters of these acrylic acids (acrylates) and the substituted acrylic acids. Commercially available polymers include those sold under the trade names CARBOPOL, ACRYSOL, POLYGEL, SOKALAN, CARBOPOL ULTREZ, and POLYGEL. Examples of commercially available carboxylic acid polymers include the carbomers, which are homopolymers of acrylic acid crosslinked with allyl ethers of sucrose or pentaerytritol. The carbomers are available as the CARBOPOL 900 series from B.F. Goodrich (e.g., CARBOPOL 954). In addition, other suitable carboxylic acid polymeric agents include ULTREZ 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as CARBOPOL 1342, CARBOPOL 1382, PEMULEN TR-1, and PEMULEN TR-2, from B.F. Goodrich.

Other suitable carboxylic acid or carboxylate polymeric agents include copolymers of acrylic acid and alkyl C5-C10 acrylate, copolymers of acrylic acid and maleic anhydride, and polyacrylate crosspolymer-6. Polyacrylate Crosspolymer-6 is aviable in the raw material known as SEPIMAX ZEN from Seppic.

Another suitable carboxylic acid or carboxylate polymeric agent includes acrylamidopropyltrimonium chloride/acrylates copolymer, a cationic acrylates copolymer (or a quaternary ammonium compound), available as a raw maerial known under the tradename of SIMULQUAT HC 305 from Seppic.

In certain embodiments, the carboxylic acid or carboxylate polymer thickening agents useful herein are those selected from carbomers, acrylates/C10-C30 alkyl acrylate crosspolymers, polyacrylate crosspolymer-6, acrylamidopropyltrimonium chloride/acrylates copolymer, and mixtures thereof.

Celluloses

Non-limiting examples of celluloses include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. In some instances, the cellulose is selected from water-soluble cellulose derivatives (for example, carboxymethyl cellulose, methyl cellulose, methylhydroxypropyl cellulose, hydroxyethyl cellulose, hydroxypropyl cellulose, cellulose sulfate sodium salt). Furthermore, in some instance, the cellulose is preferably hydroxypropylcellulose (HPC).

Polyvinylpyrrolidone (PVP) and Co-Polymers

Non-limiting examples include Polyvinylpyrrolidone (PVP), Polyvinylpyrrolidone (PVP)/vinyl acetate copolymer (PVP/VA copolymer), polyvinylpyrrolidone (PVP)/eicosene copolymer, PVP/hexadecene copolymer, etc. Commercially available polyvinylpyrrolidone includes LUVISKOL K30, K85, K90 available from BASF. Commerically available copolymers of vinylpyrrolidone and vinylacetate include LUVISKOL VA37, VA64 available from BASF; copolymers of vinylpyrrolidone, methacrylamide, and vinylimidazole (INCI: VP/Methacrylamide/Vinyl Imidazole Copolymer) is commercially available as LUVISET from BASF. In some instances, PVP and PVP/VA copolymer are preferred.

Sucrose Esters

Non-limiting examples include sucrose palmitate, sucrose cocoate, sucrose monooctanoate, sucrose monodecanoate, sucrose mono- or dilaurate, sucrose monomyristate, sucrose mono- or dipalmitate, sucrose mono- and distearate, sucrose mono-, di- or trioleate, sucrose mono- or dilinoleate, sucrose pentaoleate, sucrose hexaoleate, sucrose heptaoleate or sucrose octooleate, and mixed esters, such as sucrose palm itate/stearate, and mixtures thereof.

Polyglyceryl Esters

Non-limiting polyglycerol esters of fatty acids (polygylceryl esters) include those of the following formula:

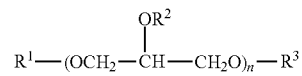

wherein n is from 2 to 20 or from 2 to 10 or from 2 to 5, or is 2, 3, 4, 5, 6, 7, 8, 9, or 10, and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$. Additionally, non-limiting examples of nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and mixtures thereof.

Gums

Non-limiting examples of gums include gum arabic, tragacanth gum, karaya gum, guar gum, gellan gum, tara gum, locust bean gum, tamarind gum, xanthan gum, locust bean gum, Seneca gum, sclerotium gum, gellan gum, etc.

pH Adjuster(s)

The cosmetic composition may include one or more pH adjusters to increase or decrease the overall pH of the cosmetic composition. For example, one or more acids may be included to decrease the pH of the cosmetic composition. Examples of suitable acids for decreasing the pH of the cosmetic composition include, but are not limited to, citric acid, acetic acid, and the like. The cosmetic composition may include one or more bases, such as sodium hydroxide, potassium hydroxide and the like, to increase the pH of the cosmetic composition. Additional or alternative acids and bases that are suitable for adjusting the pH of the cosmetic composition are readily known to one of ordinary skill in the art.

The amount of the pH adjuster in the cosmetic composition may be based on the desired pH of the final cosmetic composition and/or product. For example, the cosmetic composition may have an amount of pH adjusters such that the pH of the composition is about 3 to about 9, preferably about 4 to about 8, preferably about 5 to about 8, or preferably about 5.5 to about 8.

The amount of the pH adjuster in the cosmetic composition may be based on the desired pH of the final cosmetic composition and/or product. For example, the total amount of the pH adjuster may range from about 0.05 to about 20 wt. %, based on the total weight of the cosmetic composition. In some instances, the total amount of pH adjuster is from about 0.05 to about 15 wt. %, about 0.1 to about 10 wt. %, or about 0.12 to about 5 wt. %, including ranges and sub-ranges therebetween, based on the total weight of the cosmetic composition.

Chelating Agent(s)

The cosmetic composition may, optionally, include chelating agents. The amount of chelating agent present in the cosmetic composition may be, e.g., about 0.01 to about 20 wt. %, about 0.01 to about 15 wt. %, about 0.01 to about 10 wt. %, about 0.01 to about 8 wt. %, about 0.01 to about 6 wt. %, about 0.01 to about 5 wt. %, about 0.01 to about 4 wt. %, about 0.01 to about 3 wt. %, about 0.01 to about 2 wt. %, about 0.01 to about 1 wt. %; about 0.1 to about 20 wt. %, about 0.1 to about 15 wt. %, about 0.1 to about 10 wt. %, about 0.1 to about 8 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; about 0.25 to about 20 wt. %, about 0.25 to about 15 wt. %, about 0.25 to about 10 wt. %, about 0.25 to about 8 wt. %, about 0.25 to about 6 wt. %, about 0.25 to about 5 wt. %, about 0.25 to about 4 wt. %, about 0.25 to about 3 wt. %, about 0.25 to about 2 wt. %, about 0.25 to about 1 wt. %; about 0.5 to about 20 wt. %, about 0.5 to about 15 wt. %, about 0.5 to about 10 wt. %, about 0.5 to about 8 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; about 0.75 to about 20 wt. %, about 0.75 to about 15 wt. %, about 0.75 to about 10 wt. %, about 0.75 to about 8 wt. %, about 0.75 to about 6 wt. %, about 0.75 to about 5 wt. %, about 0.75 to about 4 wt. %, about 0.75 to about 3 wt. %, about 0.75 to about 2 wt. %; about 1 to about 20 wt. %, about 1 to about 15 wt. %, about 1 to about 10 wt. %, about 1 to about 8 wt. %, about 1 to about 6 wt. %, about 1 to about 5 wt. %, about 1 to about 4 wt. %, about 1 to about 3 wt. %, or about 1 to about 2 wt. %, including ranges and subranges therebetween, based on the total weight of the cosmetic composition.

Non-limiting examples of chemical chelating agents include aminotrimethyl phosphonic acid, β-alanine diacetic acid, cyclodextrin, cyclohexanediamine tetracetic acid, diethylenetriamine pentamethylene phosphonic acid, diethanolamine N-acetic acid, ethylene diamine tetracetic acid (EDTA or $YH_4$) and its sodium ($YH_3Na$, $Y_2H_2Na_2$, $YHNa_3$ and $YNa_4$), potassium ($YH_3K$, $Y_2H_3K_3$ and $YK_4$), calcium disodium, and diammonium salts and its salts with triethanolamine (TEA-EDTA), etidronic acid, galactanic acid, hydroxyethyl ethylenediamine tetracetic acid (HEDTA) and its trisodium salt, gluconic acid, glucuronic acid, nitrilotriacetic acid (NTA) and its trisodium salt, pentetic acid, phytic acid, ribonic acid, diammonium citrate, disodium azacycloheptane diphosphonate, disodium pyrophoshate, hydroxypropyl cyclodextrin, methyl cyclodextrin, pentapotassium triphosphate, pentasodium am inotrimethylene phosphonate, pentasodium ethylenediamine tetramethylene phosphonate, pentasodium pentetate, pentasodium triphosphate, potassium citrate, potassium EDTMP, sodium EDTMP, sodium chitosan methylene phosphonate, sodium hexametaphosphate, sodium metaphosphate, potassium polyphosphate, sodium polyphosphate, sodium trimetaphosphate, sodium dihydroxyethylglycinate, potassium gluconate, sodium gluconate, sodium glucopeptate, sodium glycereth-1 polyphosphate, tetrapotassium pyrophosphate, triethanolamine polyphosphate (TEA), tetrasodium pyrophosphate, trisodium phosphate, potassium triphosphonomethylamine oxide, sodium metasilicate, sodium phytate, sodium polydimethylglycinophenolsulfonate, tetrahydroxyethyl ethylene diamine, tetrahydroxypropyl ethylene diamine, tetrapotassium etidronate, tetrasodium etidronate, tetrasodium iminodisuccinate, trisodium ethylenediamine disuccinate, ethanolamine N,N-diacetic acid, disodium acetate, dimercaprol, deferoxamine, Zylox, and/or iron chelating agent disclosed and claimed in the international patent application WO 94/61338, which is incorporated herein in its entirety for all purposes. Examples of biological chelating agents include metallothionein, transferrin, calmodulin, and sodium chitosan methylene phosphonate. In at least one instance, the chelating agent is trisodium ethylenediamine disuccinate.

Preservative(s)

Preservatives may be included in the cosmetic composition in an amount typically from about 0.01 to about 20 wt. %, about 0.01 to about 18 wt. %, about 0.01 to about 16 wt. %, about 0.01 to about 14 wt. %, about 0.01 to about 12 wt. %, about 0.01 to about 10 wt. %, about 0.01 to about 8 wt. %, about 0.01 to about 7 wt. %, about 0.01 to about 6 wt. %, about 0.01 to about 5 wt. %; about 0.1 to about 20 wt. %, about 0.1 to about 18 wt. %, about 0.1 to about 16 wt. %, about 0.1 to about 14 wt. %, about 0.1 to about 12 wt. %, about 0.1 to about 10 wt. %, about 0.1 to about 8 wt. %, about 0.1 to about 7 wt. %, about 0.1 to about 6 wt. %, about 0.1 to about 5 wt. %; about 1 to about 20 wt. %, about 1 to about 18 wt. %, about 1 to about 16 wt. %, about 1 to about 14 wt. %, about 1 to about 12 wt. %, about 1 to about 10 wt. %, about 1 to about 8 wt. %, about 1 to about 7 wt. %, about 1 to about 6 wt. %, about 1 to about 5 wt. %; about 4 to about 20 wt. %, about 4 to about 18 wt. %, about 4 to about 16 wt. %, about 4 to about 14 wt. %, about 4 to about 12 wt. %, about 4 to about 10 wt. %, about 4 to about 8 wt. %, or about 4 to about 7 wt. %, including all ranges and sub-ranges therebetween, based on the total weight of the cosmetic composition. Non-limiting examples of preservatives include sodium benzoate, potassium sorbate, phenoxyethanol, salicylic acid, tocopherol, chlorphenesin, BHT, disodium EDTA, pentaerythrityl tetra-di-t-butyl hydroxyhydrocinnamate, and mixtures thereof.

Water

The cosmetic composition may include an amount of water that may be from about 30 to about 99.4 wt. %, based on the total weight of the cosmetic composition. In some cases, the cosmetic composition includes water in amount of about 30 to about 99.4 wt. %, about 35 to about 99.4 wt. %, about 40 to about 99.4 wt. %, about 45 to about 99.4 wt. %, about 50 to about 99.4 wt. %, about 55 to about 99.4 wt. %, about 60 to about 99.4 wt. %, about 65 to about 99.4 wt. %, about 70 to about 99.4 wt. %, about 75 to about 99.4 wt. %, about 80 to about 99.4 wt. %, about 85 to about 99.4 wt. %, about 90 to about 99.4 wt. %, about 95 to about 99.4 wt. %; about 30 to about 95 wt. %, about 35 to about 95 wt. %, about 40 to about 95 wt. %, about 45 to about 95 wt. %, about 50 to about 95 wt. %, about 55 to about 95 wt. %, about 60 to about 95 wt. %, about 65 to about 95 wt. %, about 70 to about 95 wt. %, about 75 to about 95 wt. %, about 80 to about 95 wt. %, about 85 to about 95 wt. %, about 90 to about 95 wt. %; about 30 to about 90 wt. %, about 35 to about 90 wt. %, about 40 to about 90 wt. %, about 45 to about 90 wt. %, about 50 to about 90 wt. %, about 55 to about 90 wt. %, about 60 to about 90 wt. %, about 65 to about 90 wt. %, about 70 to about 90 wt. %, about 75 to about 90 wt. %, about 80 to about 90 wt. %, about 85 to about 90 wt. %; about 30 to about 85 wt. %, about 35 to about 85 wt. %, about 40 to about 85 wt. %, about 45 to about 85 wt. %, about 50 to about 85 wt. %, about 55 to about 85 wt. %, about 60 to about 85 wt. %, about 65 to about 85 wt. %, about 70 to about 85 wt. %, about 75 to about 85 wt. %, about 80 to about 85 wt. %; about 30 to about 80 wt. %, about 35 to about 80 wt. %, about 40 to about 80 wt. %, about 45 to about 80 wt. %, about 50 to about 80 wt. %, about 55 to about 80 wt. %, about 60 to about 80 wt. %, about 65 to about 80 wt. %, about 70 to about 80 wt. %, about 75 to about 80 wt. %; about 30 to about 75 wt. %, about 35 to about 75 wt. %, about 40 to about 75 wt. %, about 45 to about 75 wt. %, about 50 to about 75 wt. %, about 55 to about 75 wt. %, about 60 to about 75 wt. %, about 65 to about 75 wt. %, about 70 to about 75 wt. %; about 30 to about 70 wt. %, about 35 to about 70 wt. %, about 40 to about 70 wt. %, about 45 to about 70 wt. %, about 50 to about 70 wt. %, about 55 to about 70 wt. %, about 60 to about 70 wt. %, about 65 to about 70 wt. %; about 30 to about 65 wt. %, about 35 to about 65 wt. %, about 40 to about 65 wt. %, about 45 to about 65 wt. %, about 50 to about 65 wt. %, about 55 to about 65 wt. %, about 60 to about 65 wt. %, including ranges and subranges therebetween, based on the total weight of the cosmetic composition.

Method of Use

The methods for removing makeup typically comprise:
(I) applying a cosmetic composition to a layer of makeup on a keratinous substrate, the cosmetic composition comprising:
 (a) about 0.1 to about 3 wt. % of a cationic surfactant grafted halloysite compound;
 (b) about 0.5 to about 10 wt. % of a nonionic surfactant a cationic surfactant, or a mixture thereof; and
 (c) water, wherein all weight percentages are based on the total weight of the cosmetic composition, and
(II) removing at least a portion of the cosmetic composition.

The cosmetic composition may be applied to and dispersed on a keratin surface by hand or using an applicator. For example, the cosmetic composition may be applied and uniformly dispersed onto a keratin surface using a brush, comb, cloth, or other fibrous material. After a period of time, at least a portion of the cosmetic composition may be removed. Typically, removal of the cosmetic composition after the period of time also removes makeup from the keratin surface. The cosmetic composition may be applied to and/or maintained on the keratin surface for at least 15 seconds, at least 30 seconds, at least 45 seconds, at least 1 minutes, at least 2 minutes, at least 3 minutes, at least 4 minutes, at least 5 minutes, at least 7.5 minutes, at least 10 minutes, at least 15 minutes, at least 20 minutes, at least 25 minutes, etc.

EMBODIMENTS OF THE DISCLOSURE

In accordance with certain aspects of the disclosure, provided is a composition comprising:

about 0.1 to about 3 wt. %, preferably about 0.1 to about 2.95 wt. %, or preferably about 0.1 to about 2.75 wt. %, of a cationic surfactant grafted halloysite compound, preferably a cationic surfactant grafted halloysite compound having a cationic surfactant portion chosen from cetyltrimethylammonium chloride, behentrimonium chloride, brassicamidopropyl dimethylamine, brassicyl isoleucinate esylate, and a mixture thereof;
 about 0.5 to about 10 wt. %, preferably about 0.5 to about 9 wt. %, more preferably about 0.5 to about 8 wt. %, of a nonionic surfactant, a cationic surfactant, or a mixture thereof; and
 water, wherein the amount of water is preferably about 30 to about 99.4 wt. % or more preferably about 40 to about 99.4 wt. %, wherein all weight percentages are based on the total weight of the cosmetic composition.

According to another aspect of the disclosure, provided is a method for producing a cosmetic composition comprising:
(I) mixing a composition at a temperature of about 50° C. or more until homogenous, wherein the composition comprises:
 about 0.1 to about 3 wt. %, preferably about 0.1 to about 2.95 wt. %, or preferably about 0.1 to about 2.75 wt. %, of a cationic surfactant grafted halloysite compound, preferably a cationic surfactant grafted halloysite compound having a cationic surfactant portion chosen from cetyltrimethylammonium chloride, behentrimonium chloride, brassicamidopropyl dimethylamine, brassicyl isoleucinate esylate, and a mixture thereof;
 about 0.5 to about 10 wt. %, preferably about 0.5 to about 9 wt. %, more preferably about 0.5 to about 8 wt. %, of a nonionic surfactant, a cationic surfactant, or a mixture thereof; and
 water, wherein the amount of water is preferably about 30 to about 99.4 wt. % or more preferably about 40 to about 99.4 wt. %,
  wherein all weight percentages are based on the total weight of the cosmetic composition, and
 (II) cooling the composition.

In accordance with a further aspect of the disclosure, provided is a method for removing makeup comprising:
(I) applying a cosmetic composition to a layer of makeup on a keratinous substrate, the cosmetic composition comprising:
 about 0.1 to about 3 wt. %, preferably about 0.1 to about 2.95 wt. %, or preferably about 0.1 to about 2.75 wt. %, of a cationic surfactant grafted halloysite compound, preferably a cationic surfactant grafted halloysite compound having a cationic surfactant portion chosen from cetyltrimethylammonium chloride, behentrimonium chloride, brassicamidopropyl dimethylamine, brassicyl isoleucinate esylate, and a mixture thereof;
 about 0.5 to about 10 wt. %, preferably about 0.5 to about 9 wt. %, more preferably about 0.5 to about 8 wt. %, of a nonionic surfactant, a cationic surfactant, or a mixture thereof; and
 water, wherein the amount of water is preferably about 30 to about 99.4 wt. % or more preferably about 40 to about 99.4 wt. %,
  wherein all weight percentages are based on the total weight of the cosmetic composition,
 (II) removing at least a portion of the cosmetic composition.

The terms "comprising," "having," and "including" are used in their open, non-limiting sense. The terms "a" and "the" are understood to encompass the plural as well as the singular. The compositions and methods of the present disclosure can comprise, consist of, or consist essentially of the essential elements and limitations of the disclosure described herein, as well as any additional or optional ingredients, components, or limitations described herein or otherwise useful.

All percentages, parts and ratios herein are based upon the total weight of the compositions of the present disclosure, unless otherwise indicated. All ranges and values disclosed herein are inclusive and combinable. The expression "inclusive" for a range of concentrations means that the limits of the range are included in the defined interval. For examples, any value or point described herein that falls within a range described herein can serve as a minimum or maximum value to derive a sub-range, etc. Furthermore, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

Other than in the operating examples, or where otherwise indicated, all numbers expressing quantities of ingredients and/or reaction conditions are to be understood as being modified in all instances by the term "about," meaning within +/−5% of the indicated number.

As used herein, the expression "at least one" is interchangeable with the expression "one or more" and thus includes individual components as well as mixtures/combinations.

The term "substantially free" or "essentially free" as used herein means that there is less than about 5% by weight of a specific material added to a composition, based on the total weight of the compositions. Nonetheless, the compositions may include less than about 2 wt. %, less than about 1 wt. %, less than about 0.5 wt. %, less than about 0.1 wt. %, less than 0.01 wt. %, or none of the specified material.

The term "active material" as used herein with respect to the percent amount of an ingredient or raw material, refers to 100% activity of the ingredient or raw material.

Throughout the disclosure, the term "a mixture thereof" may be used following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included. The salts referred to throughout the disclosure may include salts having a counter-ion such as an alkali metal, alkaline earth metal, or ammonium counter-ion. This list of counter-ions, however, is non-limiting.

"Volatile", as used herein, means having a flash point of less than about 100° C. "Non-volatile", as used herein, means having a flash point of greater than about 100° C.

The term "polymers," as defined herein, include homopolymers and copolymers formed from at least two different types of monomers.

The term "INCI" is an abbreviation of International Nomenclature of Cosmetic Ingredients, which is a system of names provided by the International Nomenclature Committee of the Personal Care Products Council to describe personal care ingredients.

All components and elements positively set forth in this disclosure can be negatively excluded from the claims. In other words, the compositions (nanoemulsions) of the instant disclosure can be free or essentially free of all components and elements positively recited throughout the instant disclosure.

Some of the various categories of components identified may overlap. In such cases where overlap may exist and the composition includes both components (or the composition includes more than two components that overlap), an overlapping compound does not represent more than one component. For example, a fatty acid may be characterized as both a nonionic surfactant and a fatty compound. If a particular composition includes both a nonionic surfactant and a fatty compound, a single fatty acid will serve as only the nonionic surfactant or as only the fatty compound (the single fatty acid does not serve as both the nonionic surfactant and the fatty compound).

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

EXAMPLES

Implementation of the present disclosure is provided by way of the following examples. The following examples serve to elucidate aspects of the technology without being limiting in nature.

Example 1

Exemplary Compositions A-N

Two sets of fourteen exemplary cosmetic compositions (Exemplary Compositions A-N) were prepared according to aspects of the disclosure. The first set of Exemplary Compositions A-N were prepared by combining and heating all of their ingredients to a temperature of 50° C. and then mixing the compositions at 50° C. until the compositions became homogenous. The second set of Exemplary Compositions A-N were prepared according to the same formulations, but were combined and mixed at a temperature of 25° C. until homogenous.

The formulations for Exemplary Compositions A-N are presented in Table 1, below.

TABLE 1

| | | US INCI name | Ex. A (wt. %) | Ex. B (wt. %) | Ex. C (wt. %) | Ex. D (wt. %) | Ex. E (wt. %) | Ex. F (wt. %) | Ex. G (wt. %) | Ex. T (wt. %) | Ex. U (wt. %) |
|---|---|---|---|---|---|---|---|---|---|---|---|
| (a) | Cationic surfactant grafted halloysite | CTAC-HALLOYSITE BTAC-HALLOYSITE | 0.2 | 0.5 | 1.5 | 0.5 | 0.5 | 0.5 | 0.5 | 0.7 | 1 |
| (b) | Nonionic Surfactant(s) | POLOXAMER 184 | 0.8-1.2 | 0.8-1.2 | 0.8-12 | 0.8-1.2 | | | 0.8-1.2 | 0.8-1.2 | 0.8-1.2 |
| | | CAPRYLYL/CAPRYL GLUCOSIDE | | | | | 0.8-1.2 | | | | |
| | Cationic Surfactant | MYRTRIMONIUM BROMIDE | 0.05-0.5 | 0.05-0.5 | 0.05-0.5 | | | 0.05-0.5 | | 0.05-0.5 | 0.05-0.5 |
| (d) | Amphoteric Surfactant | DISODIUM COCOAMPHODIACETATE | 1.1-1.7 | 1.1-1.7 | 1.1-1.7 | | | | 1.1-1.7 | 1.1-1.7 | 1.1-1.7 |
| (e) | Polyols | GLYCERIN and HEXYLENE GLYCOL | 2-4 | 2-4 | 2-4 | 2-4 | 2-4 | 2-4 | 2-4 | 2-4 | 2-4 |
| (c) | Water | WATER | QS to 100 | QS to 100 | QS to 100 | QS to 100 | QS to 100 | QS to 100 | QS to 100 | QS to 100 | QS to 100 |

| | | US INCI name | Ex. H (wt. %) | Ex. I (wt. %) | Ex. J (wt. %) | Ex. K (wt. %) | Ex. L (wt. %) | Ex. M (wt. %) | Ex. N (wt. %) |
|---|---|---|---|---|---|---|---|---|---|
| (a) | Cationic surfactant grafted halloysite | BILE-HNT BAPDMA-HNT | 0.2 | 0.5 | 1 | 3 | 0.2 | 0.5 | 1 |
| (b) | Nonionic Surfactant | POLOXAMER 184 | 0.8-1.2 | 0.8-1.2 | 0.8-1.2 | 0.8-1.2 | 0.8-1.2 | 0.8-1.2 | 0.8-1.2 |
| | Cationic Surfactant | MYRTRIMONIUM BROMIDE | 0.05-0.5 | 0.05-0.5 | 0.05-0.5 | 0.05-0.5 | 0.05-0.5 | 0.05-0.5 | 0.05-0.5 |
| (d) | Amphoteric Surfactant | DISODIUM COCOAMPHODIACETATE | 1.1-1.7 | 1.1-1.7 | 1.1-1.7 | 1.1-1.7 | 1.1-1.7 | 1.1-1.7 | 1.1-1.7 |
| (e) | Polyols | GLYCERIN and HEXYLENE GLYCOL | 2-4 | 2-4 | 2-4 | 2-4 | 2-4 | 2-4 | 2-4 |
| (c) | Water | WATER | QS to 100 | QS to 100 | QS to 100 | QS to 100 | QS to 100 | QS to 100 | QS to 100 |

Example 2

Comparative Compositions 1-6

Two sets of six comparative cosmetic compositions (Comparative Compositions 1-6) were prepared to have the formulations shown in Table 2, below. The first set of Comparative Compositions 1-6 were prepared by combining and heating all of their ingredients to a temperature of 50° C. and then mixing the compositions at 50° C. until the compositions became homogenous. The second set of Comparative Compositions 1-6 were prepared according to the same formulations, but were combined and mixed at a temperature of 25° C. until homogenous.

Example 3

Evaluation of Ex. A-N and Comp. 1-8

Exemplary Compositions A-N and Comparative Compositions 1-8 were evaluated to assess their ability to remove mascara. Comparative Compositions 7 and 8 were commercially available products having the following lists of ingredients.

Comparative Composition 7: AQUA/WATER, HEXYLENE GLYCOL, GLYCERIN, DISODIUM COCOAMPHODIACETATE, DISODIUM EDTA, POLOXAMER 184, MYTRIMONIUM BROMIDE

TABLE 2

| | | US INCI name | Comp. 1 (wt. %) | Comp. 2 (wt. %) | Comp. 3 (wt. %) | Comp. 4 (wt. %) | Comp. 5 (wt. %) | Comp. 6 (wt. %) |
|---|---|---|---|---|---|---|---|---|
| (a) | Halloysite | CTAC-HALLOYSITE | | | 3 | | 0.5 | 0.5 |
| | | HALLOYSITE (NOT TREATED) | | | | 1 | | |
| (b) | Nonionic Surfactant | POLOXAMER 184 | 0.8-1.2 | 0.8-1.2 | 0.8-1.2 | 0.8-1.2 | | |
| | Cationic Surfactant(s) | CETRIMONIUM CHLORIDE | 0 | 0 | 0.05-0.5 | 0.05-0.5 | | |
| | | MYRTRIMONIUM BROMIDE | 0.05-0.5 | 0.05-0.5 | 0.05-0.5 | 0.05-0.5 | 0.05-0.5 | 0.05-0.5 |
| (d) | Amphoteric Surfactant | DISODIUM COCOAMPHODIACETATE | 1.1-1.7 | 1.1-1.7 | 1.1-1.7 | 1.1-1.7 | 1.1-1.7 | |
| (e) | Polyols | GLYCERIN | 3 | 3 | 3 | 3 | 3 | 3 |
| (c) | Water | WATER | QS to 100 | QS to 100 | QS to 100 | QS to 100 | QS to 100 | QS to 100 |

Comparative Composition 8: WATER (AQUA), PEG-6 CAPRYLIC/CAPRIC GLYCERIDES, CUCUMIS SATIVUS (CUCUMBER) FRUIT EXTRACT, MANNITOL, XYLITOL, RHAMNOSE, FRUCTOOLIGOSACCHARIDES, PROPYLENE GLYCOL, DISODIUM EDTA, CETRIMONIUM BROMIDE To evaluate the compositions properties for removing mascara, an anhydrous water-proof mascara was applied using 30 strokes to fake eyelashes. The mascara on the fake eyelashes were allowed to dry overnight at room temperature. After drying overnight, the amount of mascara deposited on the fake eyelashes was determined.

The amount of mascara removed by Exemplary Compositions A-N and Comparative Compositions 1-8 was assess by wetting four pieces of cotton rounds each with 1 gram of a select composition. The fake eyelashes were then placed onto a piece of BIOSKIN™ (SKINFX DS8 AXONCABLE) and covered by the first piece of cotton round. 450 grams of force was loaded onto the cotton pad and then the cotton round was wiped across the fake lashes 5 times to remove mascara. The second piece of cotton round was then placed onto of the fake lashes, loaded with 450 grams of force, and wiped across the fake lashes 5 times to remove mascara. This process was repeated with the third and the fourth cotton rounds, which each had received 1 gram of the same composition. The fake eyelashes were then dried for 1 hour and weighed to determine the amount of mascara removed. The results of the evaluation are shown in Table 3, below.

TABLE 3

| Composition | Removability (cold processed) (%) | Removability (hot processed) (%) | ΔRemovability (%) |
| --- | --- | --- | --- |
| Ex. A | 26.62 | 46.20 | 73.56 |
| Ex. B | 26.83 | 56.20 | 109.47 |
| Ex. C | 39.81 | 48.00 | 20.56 |
| Ex. D | 28.00 | 52.20 | 85.77 |
| Ex. E | 32.40 | 56.90 | 75.62 |
| Ex. F | 11.10 | 26.40 | 137.8 |
| Ex. G | 30.26 | 48.30 | 59.61 |
| Ex. H | 30.7 | 60.9 | 98.5 |
| Ex. I | 29.2 | 50.3 | 72.3 |
| Ex. J | 37.1 | 54.5 | 46.9 |
| Ex. K | 29.7 | 44.6 | 50.1 |
| Ex. L | 36.8 | 62.5 | 69.9 |
| Ex. M | 29.7 | 53.1 | 79.1 |
| Ex. N | 34.0 | 48.1 | 41.6 |
| Ex. T | 33.70 | 45.90 | 36.22 |
| Ex. U | 28.97 | 45.78 | 58.03 |
| Comp. 1 | 24.74 | 22.81 | −7.82 |
| Comp. 2 | 32.79 | 29.90 | −8.81 |
| Comp. 3 | 24.70 | 22.80 | −7.69 |
| Comp. 4 | 35.90 | 35 | −2.51 |
| Comp. 5 | 32.00 | 37 | 15.63 |
| Comp. 6 | 16.80 | 12.20 | −27.4 |
| Comp. 7 | 30.2 | N/A | N/A |
| Comp. 8 | 25.00 | N/A | N/A |

Comparative Composition 2 was identified as a comparative composition because it did not exhibit a significant increase in removability when prepared at a temperature of 50° C. as compared to being prepared at a temperature of 25° C. It is currently unclear to the inventors as to the reason that Comparative Composition 2 did not exhibit a significant increase in removability when prepared at a temperature of 50° C.

Figure 2:
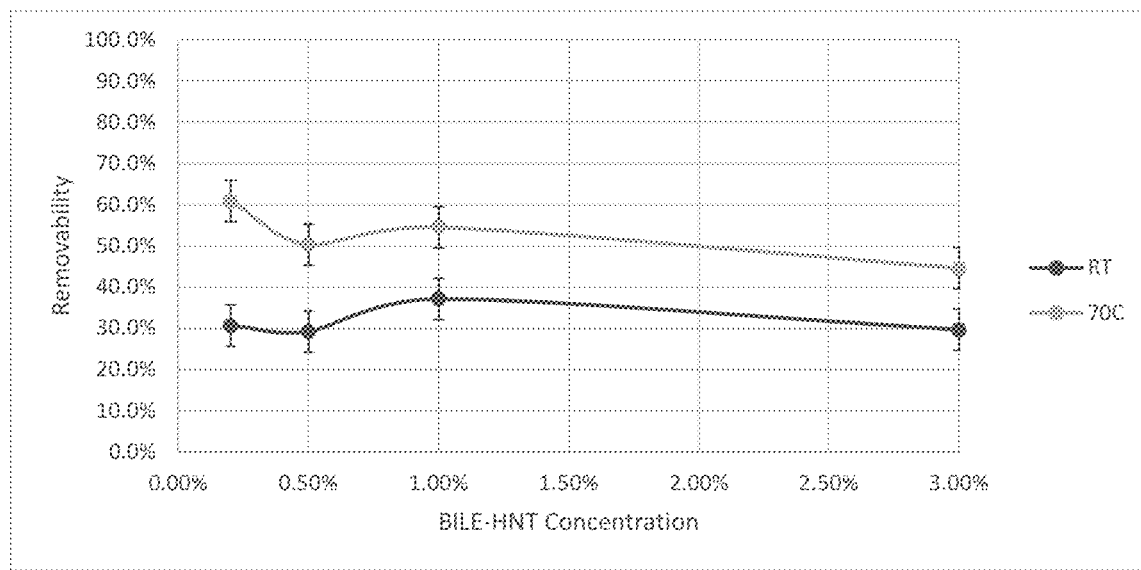
FIG. 2 is a graph illustrating the change in removability for additional, non-limiting exemplary compositions produced under different temperatures in accordance with aspects of the disclosure.
Figure 3:
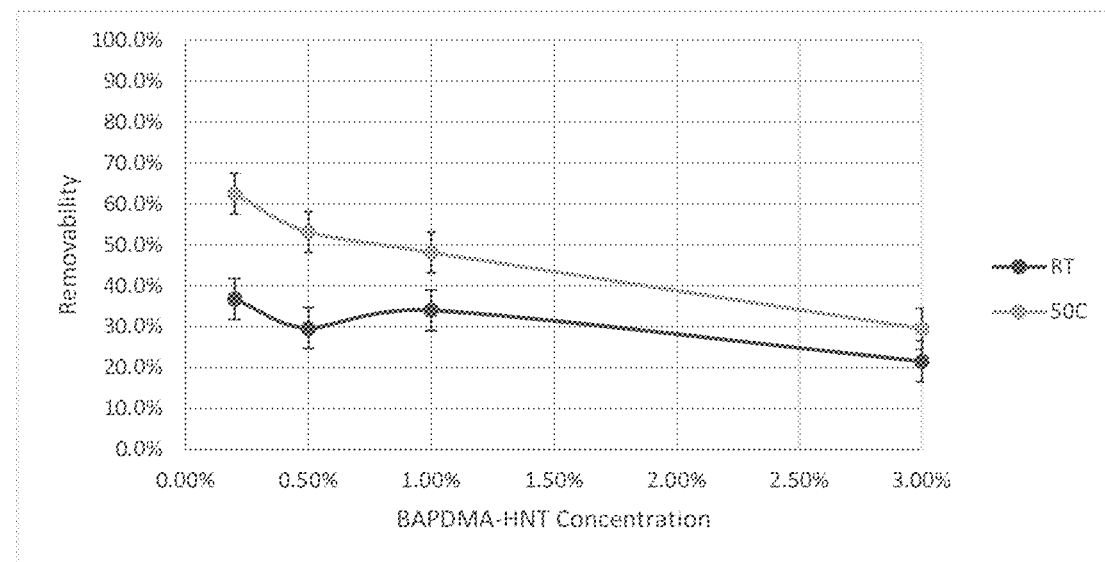
FIG. 3 is a graph illustrating the change in removability for further, non-limiting exemplary compositions produced under different temperatures according to aspects of the disclosure.

The change in removability (Δ Removability) for Exemplary Compositions A-C, T and U is shown in FIG. 1. The change in removability (Δ Removability) for Exemplary Compositions H-K is shown in FIG. 2. The change in removability (Δ Removability) for Exemplary Compositions L-N is shown in FIG. 3.

Example 4

Evaluation on Processing Temperature

Figure 4:
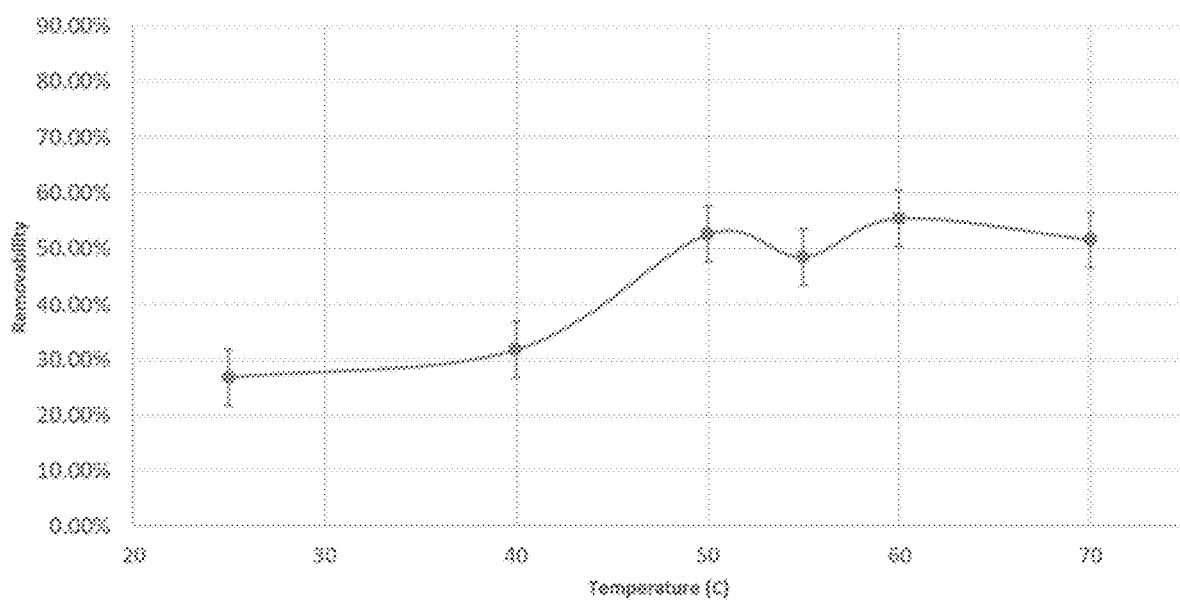
FIG. 4 is a graph illustrating the change in removability for a cosmetic composition produced under different temperatures in accordance with aspects of the disclosure.

Samples of Exemplary Composition B were prepared at different temperatures to assess the effects of the processing temperature on the compositions ability to removing mascara. Specifically, six samples of Exemplary Composition B were prepared by mixing all the ingredients at the temperatures shown in Table 5, below, until the samples were until homogenous. The amount of mascara removed by the six samples of Exemplary Composition B were assessed according to the procedure described in Example 3. The results of the evaluation of the six samples ability to remove mascara is shown in Table 4 and FIG. 4.

TABLE 4

| Sample No. of Ex. B | Processing temperature | Removability |
| --- | --- | --- |
| Sample 1 | 25 C. | 26.83% |
| Sample 2 | 40 C. | 31.80% |
| Sample 3 | 50 C. | 52.60% |
| Sample 4 | 55 C. | 48.50% |
| Sample 5 | 60 C. | 55.40% |
| Sample 6 | 70 C. | 51.60% |

Example 5

Exemplary Compositions and Evaluation Thereof

Two sets of five exemplary cosmetic compositions (Exemplary Compositions O-S) were prepared according to aspects of the disclosure. The first set of Exemplary Compositions O-S were prepared by combining and heating all of their ingredients to a temperature of 70° C. and then mixing the compositions at 70° C. until the compositions became homogenous. The second set of Exemplary Compositions O-S were prepared according to the same formulations, but were combined and mixed at a temperature of 25° C. until homogenous. The formulations for Exemplary Compositions D, E, and O-S are presented in Table 5, below.

TABLE 5

| | | US INCI name | Ex. D (wt. %) | Ex. E (wt. %) | Ex. O (wt. %) | Ex. P (wt. %) | Ex. Q (wt. %) | Ex. R (wt. %) | Ex. S (wt. %) |
| --- | --- | --- | --- | --- | --- | --- | --- | --- | --- |
| (a) | Cationic surfactant grafted halloysite | CTAC-HALLOYSITE | 0.5 | 0.5 | 0.5 | 0.5 | 0.5 | 0.5 | 0.5 |

TABLE 5-continued

| | US INCI name | Ex. D (wt. %) | Ex. E (wt. %) | Ex. O (wt. %) | Ex. P (wt. %) | Ex. Q (wt. %) | Ex. R (wt. %) | Ex. S (wt. %) |
|---|---|---|---|---|---|---|---|---|
| (b) Nonionic Surfactant(s) | POLOXAMER 184 | 0.8-1.2 | | | | | | |
| | CAPRYLYL/CAPRYL GLUCOSIDE | | 0.8-1.2 | | | | | |
| | PEG-6 CAPRYLIC/CAPRIC GLYCERIDES | | | 0.8-1.2 | | | | |
| | STEARETH-20 | | | | 0.8-1.2 | | | |
| | POLYGLYCERYL-6 CAPRATE | | | | | 0.8-1.2 | | |
| | PEG-7 GLYCERYL COCOATE | | | | | | 0.8-1.2 | |
| | POLOXAMER 182 | | | | | | | 0.8-1.2 |
| | HLB Value of Surfactants | 13.4 | 13 | 19 | 15.3 | 15 | 12 | 7 |
| (e) Polyols | GLYCERIN and HEXYLENE GLYCOL | 3 | 3 | 3 | 3 | 3 | 3 | 3 |
| (c) Water | WATER | QS to 100 | QS to 100 | QS to 100 | QS to 100 | QS to 100 | QS to 100 | QS to 100 |

Figure 5:
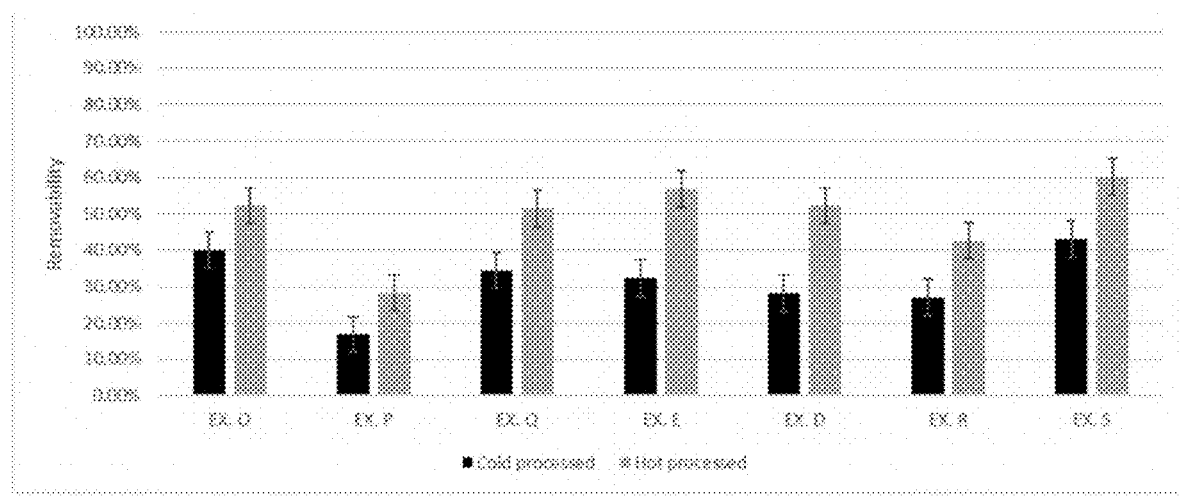
FIG. 5 is a bar graph illustrating the removability for additional compositions according to aspects of the disclosure.

The amount of mascara removed by Exemplary Compositions D, E, and O-S were assessed according to the procedure described in Example 3. The results of the evaluation of Exemplary Compositions D, E, and O-S ability to remove mascara is shown in Table 6, below, and FIG. 5.

TABLE 7

| Composition | Removability (cold processed) (%) | Removability (hot processed) (%) | ΔRemovability (%) |
|---|---|---|---|
| Ex. D | 28.00 | 52.20 | 85.77 |
| Ex. E | 32.40 | 56.90 | 75.62 |
| Ex. O | 40.10 | 52.20 | 30.17 |
| Ex. P | 16.8 | 28.30 | 68.23 |
| Ex. Q | 34.50 | 51.50 | 49.28 |
| Ex. R | 27 | 42.60 | 57.78 |
| Ex. S | 43.10 | 60.20 | 39.68 |

The invention claimed is:

1. A cosmetic composition comprising:
   (a) about 0.1 to about 3 wt. % of a cationic surfactant grafted halloysite compound;
   (b) about 0.5 to about 10 wt. % of a nonionic surfactant, a cationic surfactant, or a mixture thereof; and
   (c) water,
   wherein all weight percentages are based on the total weight of the cosmetic composition.

2. The cosmetic composition of claim 1, wherein a cationic surfactant portion of the cationic surfactant grafted halloysite is chosen from cetyltrimethylammonium chloride, behentrimonium chloride, brassicamidopropyl dimethylamine, brassicyl isoleucinate esylate, and a mixture thereof.

3. The cosmetic composition of claim 1, wherein the cationic surfactant portion of the cationic surfactant grafted halloysite is chosen from brassicamidopropyl dimethylamine, brassicyl isoleucinate esylate, and a mixture thereof.

4. The cosmetic composition of claim 1 comprising a nonionic surfactant chosen from PEG-55 propylene glycol oleate, PEG-6 propylene glycol caprylate/caprate, PEG-6 caprylic/capric glycerides, PEG-8 propylene glycol cocoate, PEG-25 propylene glycol stearate, glycereth-26 (PEG-26 Glyceryl Ether), PEG-7 glyceryl cocoate, PEG-30 glyceryl cocoate, PEG-75 lanolin, PEG-200 glyceryl stearate, PEG-120 propylene glycol stearate, PEG-120 methyl glucose dioleate, PEG-120 methyl glucose trioleate, PEG-150 pentaerythrityl tetrastearate, PEG hydrogenated castor oil, laureth-2, laureth-3, laureth-4, laureth-7, laureth-9, laureth-12, laureth-23, ceteth-10, steareth-10, steareth-2, steareth-20, steareth-100, beheneth-5, beheneth-10, oleth-10, pareth alcohols, trideceth-10, trideceth-12, C12-13 pareth-3, C12-13 pareth-23, C11-15 pareth-7, polysorbate-80, polysobate-20, PPG-5 ceteth-20, polyglyceryl-6 caprate, caprylyl/capryl glycoside, poloxamer 182, poloxamer 184, and a mixture thereof.

5. The cosmetic composition of claim 4, wherein the nonionic surfactant is chosen from PEG-6 caprylic/capric glycerides, steareth-20, polyglyceryl-6 caprate, caprylyl/capryl glycoside, poloxamer 182, poloxamer 184, PEG-7 glyceryl cocoate, and a mixture thereof.

6. The cosmetic composition of claim 1 comprising a cationic surfactant chosen from polyaminopropyl biguanide, dodecyltrimethylammonium bromide, hexadecyltrimethylammonium bromide, mytrimonium bromide, and a mixture thereof.

7. The cosmetic composition of claim 6, wherein the cationic surfactant is mytrimonium bromide.

8. The cosmetic composition of claim 1 comprising a cationic surfactant chosen from cetrimonium chloride, stearimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, stearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, and a mixture thereof.

9. The cosmetic composition of claim 1 further comprising:
   (d) about 0.05 to about 10 wt. % an amphoteric surfactant chosen from disodium cocoamphodiacetate, disodium lauroamphodiacetate, disodium caprylamphodiacetate, disodium caprylamphodiacetate, disodium cocoamphodipropionate, disodium lauroamphodipropionate, disodium caprylampho-dipropionate, disodium caprylomphodipropionate, lauroamphodipropionic acid, cocoamphodipropionic acid, and a mixture thereof.

10. The cosmetic composition of claim 1 being substantially free of oil.

11. The cosmetic composition of claim 1 being substantially free of anionic surfactants.

12. The cosmetic composition of claim 1 further comprising:
(e) about 0.1 to about 20 wt. % of a polyol.

13. The cosmetic composition of claim 12, wherein the polyol is chosen from glycerin, propylene glycol, butylene glycol, pentylene glycol, hexylene glycol, and a mixture thereof.

14. The cosmetic composition of claim 1 prepared by mixing all of the ingredients at a temperature of about 50° C. or more until homogenous.

15. A method for removing makeup comprising:
(I) applying a cosmetic composition to a layer of makeup on a keratinous substrate, the cosmetic composition comprising:
    (a) about 0.1 to about 3 wt. % of a cationic surfactant grafted halloysite compound;
    (b) about 0.5 to about 10 wt. % of a nonionic surfactant; and
    (c) water,
    wherein all weight percentages are based on the total weight of the cosmetic composition, and
(II) removing at least a portion of the cosmetic composition.

16. The cosmetic composition of claim 15, wherein cationic surfactant portion of the cationic surfactant grafted halloysite is chosen from cetyltrimethylammonium chloride, behentrimonium chloride, brassicamidopropyl dimethylamine, brassicyl isoleucinate esylate, and a mixture thereof.

17. The cosmetic composition of claim 16, wherein the cationic surfactant portion of the cationic surfactant grafted halloysite is chosen from brassicamidopropyl dimethylamine, brassicyl isoleucinate esylate, and a mixture thereof.

18. A method for producing a cosmetic composition comprising:
(I) mixing a composition at a temperature of about 50° C. or more until homogenous, wherein the composition comprises:
    (a) about 0.1 up to 3 wt. % of a cationic surfactant grafted halloysite compound;
    (b) about 0.5 to about 10 wt. % of a nonionic surfactant, a cationic surfactant, or a mixture thereof; and
    (c) water, wherein all weight percentages are based on the total weight of the cosmetic composition, and
(II) cooling the composition.

19. The method of claim 18, wherein the composition is mixed at a temperature of about 50 to about 100° C.

20. The cosmetic composition of claim 18, wherein cationic surfactant portion of the cationic surfactant grafted halloysite is chosen from cetyltrimethylammonium chloride, behentrimonium chloride, brassicamidopropyl dimethylamine, brassicyl isoleucinate esylate, and a mixture thereof.

* * * * *